United States Patent
Chen et al.

[11] Patent Number: 5,808,064
[45] Date of Patent: Sep. 15, 1998

[54] PALLADIUM CATALYZED INDOLIZATION

[75] Inventors: Cheng-Yi Chen, Colonia; Robert D. Larsen, Bridgewater, both of N.J.

[73] Assignee: Merck & Co., Inc., Rahway, N.J.

[21] Appl. No.: 908,683

[22] Filed: Aug. 7, 1997

Related U.S. Application Data

[60] Provisional application No. 60/023,860, Aug. 13, 1996, and provisional application No. 60/030,155, Oct. 31, 1996.

[51] Int. Cl.$^6$ ............... C07D 413/12; C07D 209/04
[52] U.S. Cl. ............... 544/132; 544/364; 544/366.6; 544/369; 546/187; 546/201; 546/272.4; 548/229; 548/266.4; 548/312.1; 548/465; 548/466; 548/467; 548/405
[58] Field of Search ............... 548/229, 266.4, 548/312.1, 465, 466, 467, 405; 546/187, 201, 272.4; 544/132, 364, 366, 369

[56] References Cited

U.S. PATENT DOCUMENTS

| 5,298,520 | 3/1994 | Baker et al. ............... 514/383 |
| 5,567,824 | 10/1996 | Chen et al. ............... 548/252 |

FOREIGN PATENT DOCUMENTS

| 0 497 512 | 5/1992 | European Pat. Off. . |
| 0 548 813 A1 | 6/1993 | European Pat. Off. . |
| WO 94/02476 | 3/1994 | WIPO . |
| WO 95/32197 | 11/1995 | WIPO . |

OTHER PUBLICATIONS

Murakami, M. et al., "The Journal of Organic Chemistry", 1988, 53, pp. 4158–4159.
Brook, A. G., et al., Chem. Abs., vol. 89, No. 25, Abs. No. 215478K, 1978.
Iritani, K., et al., Tetrahedron Letters, vol. 29, pp. 1799–1802, 1988.
Chen, C. Y., et al., J. Of Organic Chemistry, pp. 2676–2677, 1997.
Astleford, et al. "Synthesis of 1–Alkyl . . . " J. Org. Chem. vol. 54, pp. 731–732, 1989.
Wensbo, et al. "Palladium–Catalysed Synthesis of Hetero-condensed Pyrroles" Tetrahedron Letters, vol. 34, No. 17 pp. 2823–2826, 1993.
Jeschke et al, "A Novel Approach to Bz–Substituted Tryptophans . . . " Tetrahedron Letters, vol. 34, No. 40, pp. 6471–6474 (1993).
Larock et al., "Synthesis of Indoles via Palladium . . . " J. Am. Chem. Soc., vol. 113, pp. 6689–6690 (1991).
Luo et al., "Heterocycles" Chemical Abstracts, vol. 116, No. 19, AB. No. 194092, 1991.
Chen et al., Tetrahedron Letters, vol. 35, No. 38, pp. 6981–6984 (1994). "Synthesis of the 5 HTID Receptor Agonist . . . ".

Chen et al., "Improved Fischer Indole Reaction . . . " J. Org. Chem. vol. 59, 3738 (1994).
Iida et al., "Intramolecular Cyclization of Enaminones. . . " J. Org. Chem. vol. 45, 2938–2942 (1980).
Sakamoto, et al., "Condensed Heteroaromatic Ring Systems . . . " Synthesis, pp. 215–218, (1990).

*Primary Examiner*—Joseph K. McKane
*Attorney, Agent, or Firm*—Philippe L. Durette; Melvin Winokur

[57] ABSTRACT

We have found that 2-unsubstituted indoles of structural formula (IV) can be cost-effectively synthesized in high yield by the palladium-catalyzed coupling/ring closure of a 2-halo or 2-trifluoromethylsulfonyloxy aniline (I) and an acyl silane derivative (II), followed by deprotection of the silyl protecting groups.

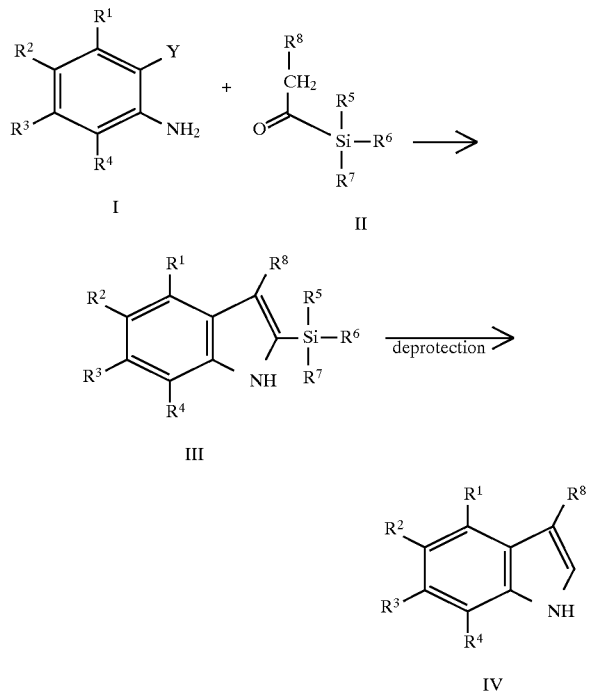

The process of the present invention is particularly useful to form indoles containing acid-labile substituents such as triazole, acetyl, ketal, cyano, and carbamate, or indoles having a good leaving group in the benzyl position. The advantages of the present process are that it does not require the use of triphenyl phosphine or tetrabutyl ammonium chloride or lithium chloride. When applied to 5-triazolyl substituted indoles, the present process also eliminates the tendency of triazolyl polymerization in the Fischer indole synthesis.

20 Claims, No Drawings

PALLADIUM CATALYZED INDOLIZATION

This application is based on provisional application 60/023,860 filed Aug. 13, 1996 and provisional application 60/030,155 filed Oct. 31, 1996.

BACKGROUND OF THE INVENTION

The present invention relates to the preparation of 2-silyl protected indoles from the palladium catalyzed reaction of halo-anilines and acyl silanes (which act as aldehyde synthons). These 2-silyl derivitives may, according to the present invention, be converted to the corresponding 2-unsubstituted indole derivative. The present invention is particularly useful in the preparation of 5-heterocyclic substituted tryptamines such as 5-(1,2,4-triazol-1-yl) tryptamine. These compounds are therapeutically active as anti-migraine agents.

Generally, indoles are prepared via the Fischer-indole reaction. For example, Chen et al., *J. Org. Chem.*, 59:3738 (1994) disclose the preparation of N,N-dimethyl tryptamines from 4-substituted hydrazines and dimethylaminobutyraldehyde dimethyl acetal using 4% $H_2SO_4$. However, the yields are often low, particularly for compounds having triazole substitution. Benzyltriazoles are unstable to the Fischer indole reaction conditions, which generally lead to polymerization of the triazole moiety, and the production of oligomers.

Larock et al., *J. Am. Chem. Soc.*, 113:6689 (1991) have shown that coupling of an iodoaniline species with an internal acetylene using palladium catalysis gives 2,3-disubstituted indoles in good-to-excellent yields. Smith et al., have also demonstrated this for 4-pyrimidinyl and pyridinyl derivatives of indol-3-yl-alkyl piperazines as in published EPO 548 831 A1. Two other applications of this methodology have been demonstrated in the syntheses of heterocondensed pyrroles and tryptophans. See Wensbo et al., *Tetrahedron Lett.*, 34:2823 (1993); Wensbo et al., *Tetrahedron Lett.*, 34:6471 (1993). However, all of these methods require triphenylphosphine, as part of the catalyst system, which is an environmental hazard. An alternate process has been developed to overcome the low yield of the Fischer-indole reaction with certain starting materials and to avoid the use of the environmentally hazardous triphenylphosphine. This process is detailed in PCT publication WO 95/32197 and involves the palladiumcatalyzed coupling/ring closure of a 3-iodo-4-aminobenzyltriazole with a suitably protected butynol derivative to the corresponding tryptophol, followed by conversion of the hydroxyethyl moiety to a dimethyl amino ethyl; as shown below:

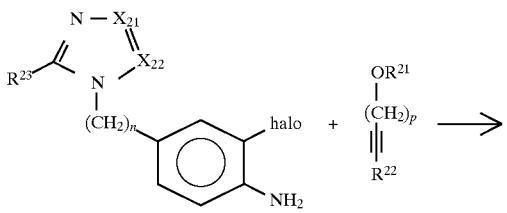

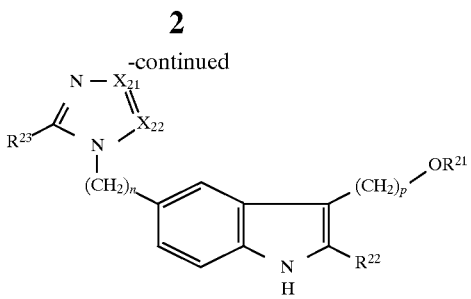

said process being carried out in a dry inert organic solvent for the starting materials at a temperature in the range of about 70° to 120° C., in the presence of a palladium catalyst, and in the presence of an inorganic or organic amine compound, wherein:

$X_{21}$ and $X_{22}$ are independently ring nitrogen or carbon atoms;

halo represents Br or I;

n is an integer from 0–1;

p is an integer from 1–4;

$R^{23}$ is H or linear or branched $C_1$–$C_4$ alkyl;

$R^{21}$ is H or a radical with functions as a hydroxy protecting group, which is removable, under mild acid hydrolyses, for example, by contacting with a mixture of HCl/MeOH, e.g. 1:1 2N HCl/MeOH at 0°–30° C., and $R^{22}$ is a radical which functions as a terminal acetylene carbon protecting group.

However, although the chemistry of this alternate process is effective, the starting materials, butynol and triethylsilyl chloride, are relatively expensive. The present invention provides for a cost-effective indolization procedure.

Iida et al., *J. Org. Chem.* 45:2938–2942 (1980) describe intramolecular cyclization of 3-((2-bromoaryl)amino) cyclohex-2-en-1-ones with catalytic palladium in the presence of triphenyl phosphine, as well as the reaction of aryl amines with β-diketones to form the corresponding secondary enaminone followed by N-ethylation to form the corresponding tertiary enaminones and subsequent intramolecular cyclization in the presence of equimolar palladium acetate.

Sakamota et al., Synthesis, p. 215–218 (1990), describe palladium-catalyzed cyclization of β-(2-halophenyl)amino substituted αβ-unsaturated ketones and esters to produce 2,3-disubstituted indoles. The procedure of Sakamota et al., also employs phosphine.

The present invention has particular application in the synthesis of $5HT_{1D}$ receptor agonists. These agonists mimic the effects of the neurotransmitter serotonin which acts as a vasoconstrictor in the brain. $5HT_{1D}$ receptor agonists display beneficial properties in migraine therapies. Over the past few years an extensive effort has been devoted to the development of N,N-dialkyltryptamines as $5\text{-}HT_{1D}$ receptor agonists to achieve the desired activity and selectivity for the treatment of migraine. Sumatriptan is the first of this class of drugs to be approved for this purpose. MK-0462 (developed by Merck & Co.), is described in U.S. Pat. No. 5,298,520 and is also a potent $5\text{-}HT_{1D}$ receptor agonist that is undergoing clinical studies.

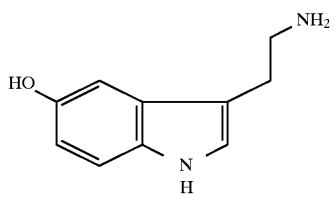

Serotonin (5-HT)

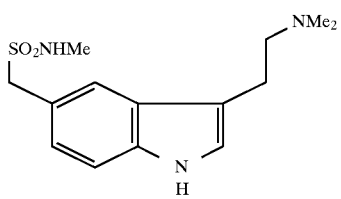

Sumatriptan

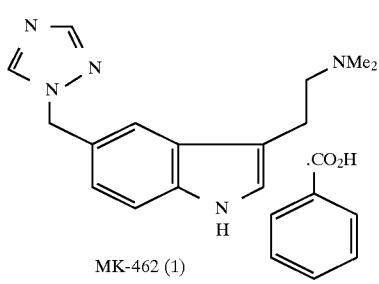

MK-462 (1)

Thus, the present invention also provides for an efficient and cost-effective synthesis of 5-heterocyclic-substituted tryptamines useful in the treatment of migraine headaches.

SUMMARY OF THE INVENTION

We have found that 2-unsubstituted indoles can be cost-effectively synthesized in high yield by the palladium-catalyzed coupling/ring closure of a 2-halo or 2-trifluoromethylsulfonyloxy (OTf)— aniline and an acyl silane derivative, followed by deprotection of the silyl protecting groups. The process of the present invention is particularly useful to form indoles containing acid-labile substituents such as triazole, acetyl, ketal, cyano, and carbamate, or indoles having a good leaving group in the benzyl position. The advantages to the present process are that it does not require the use of triphenylphosphine or tetrabutyl ammonium chloride or lithium chloride. When applied to 5-triazolyl substituted indoles, the present process also eliminates the tendency of triazolyl polymerization in the Fischer indole synthesis.

By this invention, there is provided a process comprising the step of contacting a compound of Structure I with a compound of Structure II to form a compound of Structure III:

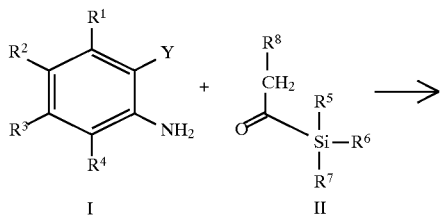

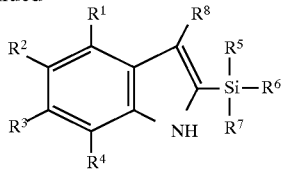

III wherein Y is selected from Br, I, and triflate, and
$R^1$, $R^2$, $R^3$, $R^4$, and $R^8$ are each substituents that will not interfere with the reaction conditions, and
$R^5$, $R^6$, and $R^7$ each represent $C_{1-6}$ alkyl, $OC_{1-6}$ alkyl, or phenyl.

More particularly, the present invention relates to the reaction above wherein:

Y is selected from Br, I and triflate;
$R^1$, $R^2$, $R^3$ and $R^4$ are each independently selected from:
(1) hydrogen;

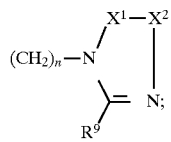

(3) $C_{1-6}$ alkyl;
(4) —$(CH_2)_n$—Z
wherein Z represents:
(a) hydrogen,
(b) halogen,
(c) cyano,
(d) nitro,
(e) trifluoromethyl,
(f) —$OR^{10}$,
(g) —$OCOR^{10}$,
(h) —$OCONR^{10}R^{11}$,
(i) —$OCH_2CN$,
(j) —$OCH_2CONR^{10}R^{11}$,
(k) —$SR^{10}$, provided that $R^{10}$ is not hydrogen,
(l) —$SOR^{10}$,
(m) —$SO_2R^{10}$,
(n) —$SO_2NR^{10}R^{11}$,
(o) —$NR^{10}R^{11}$,
(p) —$NR^{10}COR^{11}$,
(q) —$NR^{10}CO_2R^{11}$,
(r) —$NR^{10}SO_2R^{11}$,
(s) —$COR^{10}$,
(t) —$CO_2R^{10}$,
(u) —$CONR^{10}R^{11}$,
or Z is a group of formula (Za), (Zb), (Zc), or (Zd):

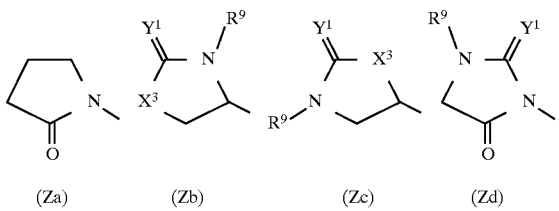

(Za)   (Zb)   (Zc)   (Zd)

or Z represents an optionally substituted five-membered heteroaromatic ring selected from furan, thiophene, pyrrole, oxazole, thiazole, isoxazole, isothiazole, imidazole, pyrazole, oxadiazole, thiadiazole, triazole and tetrazole;

$R^5$, $R^6$, and $R^7$ are each independently selected from:
(1) $C_{1-6}$ alkyl,
(2) —O—$C_{1-6}$ alkyl, and
(3) phenyl;

$R^8$ is selected from:
(1) hydrogen,
(2) —$R^{19}$—OH,
(3) —$R^{19}$—O—$R^{17}$, and
(4) —$R^{19}NR^{12}R^3$, and
(5) —$R^{19}$—$Z^1$
    wherein: $Z^1$ is a 3 to 7 membered heterocyclic ring wherein the ring members are selected from 1 to 2 nitrogen atoms and wherein the heterocyclic ring may be subsituted by one or more $R^{14}$;

$R^9$ is selected from:
(1) hydrogen, and
(2) $C_{1-4}$ alkyl;

$R^{10}$ and $R^{11}$ are each independently selected from:
(1) hydrogen,
(2) $C_{1-6}$ alkyl,
(3) trifluoromethyl,
(4) phenyl, optionally substituted with one or more $R^{20}$ substituents
(5) methylphenyl, optionally substituted with one or more $R^{20}$ substituents, and
(6) an aryl$C_{1-6}$alkyl- or heteroaryl $C_{1-6}$alkyl-group. optionally substituted with one or more $R^{20}$ substituents, or
$R^{10}$ and $R^{11}$ when linked through a nitrogen atom, together represent the residue of an optionally substituted azetidine, pyrrolidine, piperidine, morpholine or piperazine ring, optionally substituted with one or more $R^{18}$ substituents;

$R^{12}$ and $R^{13}$ are each independently selected from:
(1) $C_{1-4}$ alkyl,
(2) $C_6$aryl-$C_{1-4}$ alkyl- wherein aryl may be unsubstituted or substituted with one to three substituents selected from methyl, halo, and halomethyl, $R^{14}$ is selected from:
(1) aryl-$C_{1-6}$alkyl-, unsubstituted or substituted with one to three $R^{20}$ substitutents, and
(2) heteroaryl-$C_{1-6}$alkyl-, unsubstituted or substituted with one to three $R^{20}$ substitutents, $R^{15}$ and $R^{16}$ are each independently selected from
(1) hydrogen,
(2) $C_{1-6}$alkyl,
(3) $C_{3-7}$cycloalkyl,
(4) $C_{3-7}$cycloalkyl$C_{1-6}$alkyl-,
(5) indanyl,
(6) aryl,
(7) aryl$C_{1-6}$alkyl-,
(8) $C_{3-7}$heterocycloalkyl-,
(9) $C_{3-7}$heterocycloalkyl$C_{1-6}$alkyl-,
(10) heteroaryl, and
(11) heteroaryl$C_{1-6}$alkyl-;

$R^{17}$ is selected from a hydroxy protecting group that is removable under mild acid hydrolysis;

$R^{18}$ is selected from:
(1) $C_{1-6}$alkyl-,
(2) aryl$C_{1-6}$alkyl-,
(3) $C_{1-6}$alkoxy-,
(4) $C_{2-6}$alkyoxycarbonyl-, and
(5) $C_{1-6}$alkylaminocarbonyl-;

$R^{19}$ is a straight or branched $C_{1-6}$alkyl chain;

$R^{20}$ is selected from:
(1) fluoro,
(2) cyano,
(3) trifluoromethyl,
(4) $C_{1-6}$alkyl,
(5) halo$C_{1-6}$alkyl-,
(6) aryl,
(7) triazolyl,
(8) tetrazolyl,
(9) tetrazolyl-$C_{1-6}$alkyl-,
(10) hydroxy,
(11) $C_{1-6}$alkoxy-,
(12) $C_{1-6}$alkylthio-,
(13) $C_{2-6}$alkoxycarbonyl-,
(14) $C_{2-6}$alkylcarbonyl-,
(15) $C_{1-6}$alkylsulphonyl-,
(16) arylsulfonyl-,
(17) $C_{2-6}$alkylcarbonylamino-,
(18) arylcarbonylamino-,
(19) $C_{2-6}$alkoxycarbonylamino-,
(20) N—$C_{1-6}$alkyl-N—$C_{2-6}$alkoxyamino-,
(21) carbonylamino-,
(22) mono- or diarylaminocarbonylamino-,
(23) pyrrolidinylcarbonylamino-,
(24) piperidinylcarbonylamino-,
(25) aminocarbonyl-,
(26) aminocarbonylamino-,
(27) $C_{1-6}$alkylaminocarbonyl-,
(28) $C_{1-6}$alkylaminocarbonylamino-,
(29) di$C_{1-6}$alkylaminocarbonyl-,
(30) di$C_{1-6}$alkylaminocarbonylamino-,
(31) pyrrolidinylcarbonylamino-,
(32) piperidinylcarbonylamino-,
(33) aminosulfonyl-,
(34) $C_{1-6}$alkylaminosulfonyl-,
(35) $C_{1-6}$alkylsulfonylamino-,
(36) $C_{1-6}$alkylsulfonylaminomethyl-,
(37) arylsulfonylamino-,
(38) di$C_{1-6}$alkylaminosulfonyl-,
(39) aminosulphonylmethyl-,
(40) $C_{1-6}$alkylaminosulfonylmethyl-,
(41) di$C_{1-6}$alkylaminosulfonylmethyl-,
(42) —$(CH_2)_m OR^{15}$,
(43) —$(CH_2)_m SR^{15}$, provided that $R^{15}$ is not hydrogen,
(44) —$(CH_2)_m SOR^{15}$,
(45) —$(CH_2)_m SO_2 R^{15}$,
(46) —$(CH_2)_m NR^{15} R^{16}$,
(47) =O, and

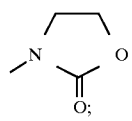

$X^1$ and $X^2$ are each independently selected from ring nitrogen or ring carbon atoms;

$X^3$ is selected from the group consisting of oxygen, sulfur, —NH— or methylene;

$Y^1$ is oxygen or sulfur;

n is an integer independently selected at each occurrence from 0 and 1;

m is an integer selected independently at each occurrence from 0 to 4; and p is an integer from 0 to 3.

The process is preferably carried out in a dry organic solvent inert for the starting materials at a temperature range of 90° to 120° C. in the presence of a palladium catalyst, and in the presence of a proton acceptor which may be an inorganic or organic amine compound.

Where Z in the compounds of formulae I and III above represents a five-membered heteroaromatic ring, this ring may be optionally substituted by one or, where possible, two substituents. As will be appreciated, where Z represents oxadiazole, thiadiazole or tetrazole ring, only one subsitutent will be possible; otherwise, one or two optional substituents may be accommodated around the five-membered heteroaromatic ring Z. Examples of suitable substituents on the five-membered heteroaromatic ring Z include $C_{1-6}$ alkyl, $C_{2-6}$alkenyl, $C_{2-6}$alkynyl, $C_{3-7}$ cycloalkyl, aryl, aryl $C_{1-6}$alkyl, $C_{3-7}$ heterocycloalkyl, heteroaryl, $C_{1-6}$alkoxy, $C_{1-6}$alkylthio, amino, $C_{1-6}$alkylamino, di$C_{1-6}$alkylamino, halogen, cyano, and trifluoromethyl.

Further, the present invention relates to deprotecting the compound of structural formula III to obtain the 2-unsubstituted indole of structural formula IV:

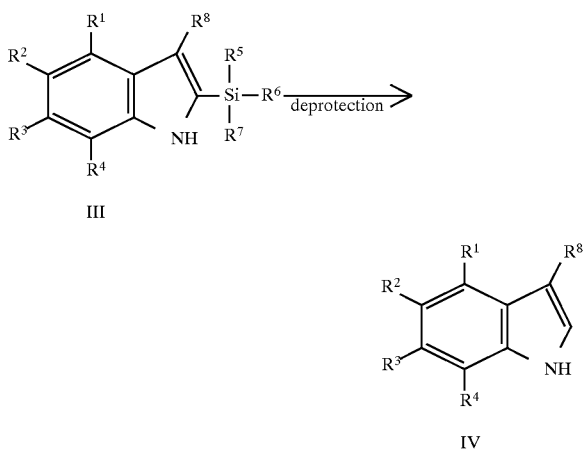

wherein $R^1$, $R^2$, $R^3$, $R^4$, $R^5$, $R^6$, $R^7$, and $R^8$ are as defined above.

Still further, the present invention is also directed to the novel intermediates of structural formulae (V) and (VI).

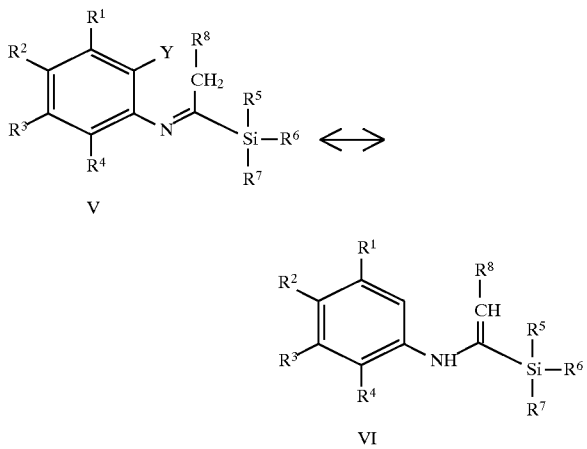

DETAILED DESCRIPTION OF THE INVENTION

Combinations of substituents and/or variables are permissible only if such combinations result in stable compounds.

In one embodiment of the present invention, $R^1$, $R^3$, and $R^4$ are each hydrogen and $R^2$, $R^5$, $R^6$, $R^7$, $R^8$, and Y are as defined above. Representative examples of $Si(R^5)(R^6)(R^7)$ radicals include trimethyl silyl, triethyl silyl, tributyl silyl, triphenyl silyl, dimethyl-t-butyl silyl, dimethylphenyl silyl, diphenylmethyl silyl, triisopropyl silyl, and the like, as well as any mixture of —$Si(OC_{1-6}$ alkyl$)_{3-n}(C_{1-6}$ alkyl$)_n$, where n is 0, 1, or 2.

$R^{17}$ acts as a protecting group for the hydroxyl group and may have the structure $Si(R^5)(R^6)(R^7)$, as described above.

The term "triflate" or "OTf" refers to the trifluoromethane sulfonyloxy group.

When an amine is included as a substituent on a compound in the present invention, in order to optimize the conditions of the reaction and to obtain better yields, the amine may have to be protected, as is known in the art, and the protecting group removed following the coupling reaction.

When a carbonyl group is included as a substituent on a compound in the present invention, in order to optimize the conditions of the reaction and to obtain better yields, the carbonyl group may have to be protected, as is known in the art, and the protecting group removed following the coupling reaction.

When an alkenyl or alkynyl group is included as a substituent on a compound in the present invention, in order optimize the conditions of the reaction and obtain better yields, the alkenyl or alkynyl group may be protected by conversion to an oxide, followed by reduction. Alternatively, an additional elimination strategy may be employed.

As used herein "alkyl", particularly the expression "$C_{1-6}$ alkyl", includes methyl and ethyl groups and straight chained or branched propyl, butyl, pentyl and hexyl groups. Particular alkyl groups are methyl, ethyl, n-propyl, isopropyl and t-butyl. Derived expressions such as $C_{1-6}$alkyoxy, $C_{1-6}$alkylthio, and $C_{1-6}$alkyl amino are to be construed accordingly.

The expression "$C_{2-6}$alkenyl" as used herein refers to straight chained and branched alkenyl groups containing from 2 to 6 carbon atoms. Typical examples include vinyl, allyl, dimethylallyl and butenyl groups.

The expression "$C_{2-6}$alkynyl" as used herein refers to straight-chained and branched alkynyl groups containing from 2 to 6 carbon atoms. Typical examples include ethynyl and propargyl groups.

Typical $C_{3-7}$cycloalkyl groups include cyclopropyl, cyclobutyl, cyclopentyl and cyclohexyl.

Typical aryl groups include phenyl and naphthyl. More particularly, aryl is phenyl.

Particular indanyl groups include indan-1-yl and indan-2-yl.

Particular aryl$C_{1-6}$alkyl groups include benzyl, phenylethyl, phenylpropyl and naphthylmethyl.

Suitable heterocycloalkyl groups include azetidinyl, pyrrolidinyl, piperidinyl, piperazinyl and morpholinyl.

Suitable heteroaryl groups include pyridyl, quinolyl, isoquinolyl, pyridazinyl, pyrimidinyl, pyrazinyl, pyranyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl, and tetrazolyl groups.

The expression "heteroaryl $C_{1-6}$alkyl" as used herein includes furylmethyl, furylethyl, thienylmethyl, thienylethyl, oxazolylmethyl, oxazolylethyl, thiazolylmethyl, thiazolylethyl., imidazolylmethyl, imidazolylethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridylmethyl, pyridylethyl, pyridinylmethyl, pyrazinylmethyl, quinolylmethyl, and isoquinolylmethyl.

The term "halogen" as used herein includes fluorine, chlorine, bromine and iodine, especially fluorine, unless otherwise specified.

The process of the present invention is preferably carried out in a dry organic solvent inert for the starting materials in the presence of a palladium catalyst, and in the presence of an inorganic or organic base which is not a "catalyst poison". Preferably, the present process is carried out at an elevated temperature.

In the process of the present invention, Structure I is coupled with Structure II to form Structure III via a palladium catalyzed reaction in a dry inert organic solvent containing a soluble palladium catalyst and in the presence of a proton acceptor, being an aromatic amine, alkylamine or inorganic base, which is not a "catalyst poison," at a temperature of about 90°–120° C.

The organic solvent useful in the process of the present invention must be one in which Structure I, Structure II and the palladium catalyst are soluble and compatible and is chemically inert under the reaction conditions. Preferred are DMSO (dimethylsulfoxide) and amide solvents such as DMF (N,N-dimethylformamide), DMAC (N,N-dimethylacetamide), and NMP (N-methyl-pyrrolidinone). Most preferred is DMF.

The acyl silane of structural formula (II) is generally employed in excess based on the the 2-halo or 2-(OTf)— aniline of structural formula (I). A useful range is about 1.0 to 3 fold, based on the 2-halo or 2-(OTf)— aniline of structural formula I. The acyl silane may be favorably employed at a two-fold excess, based on the 2-halo or 2-(OTf)— aniline of structural formula I.

The proton acceptor useful in the process of the present invention is a basic compound which can be organic or inorganic and acts as a proton acceptor and is not a "catalyst poison". By the term "catalyst poison" is meant interaction with the catalyst to inhibit its catalytic activity and prevent the coupling/ring closure between structures I and II from occurring. Suitable classes of proton acceptors include alkylamines, aromatic amines, heterocyclic amines, phosphates and the like. Alkylamines are the preferred proton acceptor in the process of the present invention. Particular alkylamines that may be employed include: DABCO (1,4-diazabicyclo[2.2.2]octane), quinuclidine, t- butylamine, 2,2,6,6,-tetramethylpiperidine and di-t-butyl-amine. DABCO is particularly preferred because it reduces the appearance of impurities in the reaction because it is resistant to oxidation to the imine in the reaction conditions of the process of the present invention.

The proton acceptor is generally employed in excess based on the the 2-halo or 2-(OTf)— aniline of structural formula (I). A useful range is about 2 to 4 fold excess, based on the 2-halo or 2-(OTf)— aniline of structural formula (1). The proton acceptor may be favorably employed at a three-fold excess, based on the 2-halo or 2-(OTf)— aniline of structural formula (I).

The palladium catalyst useful in the reaction can be selected from the following classes: Pd alkanoates, Pd acetonates, Pd halides, Pd halide complexes, Pd-benzylidine acetone complexes, as well as triaryl Pd phosphine complexes. Representative examples include, but are not limited to: Pd(II) acetate, Pd(II) acetylacetonate, Pd(O)bis-dibenzylidene acetone ("dba"), Pd(II) bromide, Pd(II) chloride, Pd(II) iodide, Pd(II) sulfate, Pd(II)trifluoroacetate, Pd(II) Cl$_2$(CH$_3$CN)$_2$, Pd$_2$ (dba)$_3$, and Pd(II)Cl$_2$(PhCN)$_2$. A useful catalyst is palladium acetate.

The palladium catalyst is employed in an amount of about 0.5 to 5 mole percent based on the halo aniline of structural formula I. A useful range is about 2 to 3 mole percent of soluble palladium catalyst, based on the halo aniline of structural formula I.

A dehydrating agent, such as magnesium sulfate may also be favorably employed in the process of coupling Structure I with Structure II to form Structure m according to the present invention. Although not necessary to the process, a dehydrating agent can assist the enamine formation by removal of the water of condensation.

The reaction is carried out in the temperature range of 90° to 120° C. A useful temperature is about 100°–105° C. Generally, the reaction is carried out under a dry, inert atmosphere at atmospheric pressure. It is useful to carry out the reaction under a nitrogen atmosphere.

The progress of the reaction may be monitored by means known in the art, including thin-layer silica gel chromatography (TLC), high pressure liquid chromatography (HPLC), gas chromatography (GC), and nuclear magnetic resonance spectroscopy (NMR). Preferably HPLC or TLC is employed, most preferably HPLC. When the reaction is complete, generally in 8 to 72 hours, the reaction mixture is cooled to room temperature and the product is separated by traditional means, e.g. by taking up with organic solvent, such as isopropyl acetate and washing with water and/or other aqueous solutions. The product may then be purified by means known in the art, including preparative thin-layer silica gel chromatography, silica gel chromatography, HPLC, crystallization, and solid-phase extraction. Preferably, the product is purified by silica gel chromatography or crystallization.

Further, the present invention relates to deprotecting the compound of structural formula III to obtain the 2-unsubstituted indole of structural formula IV:

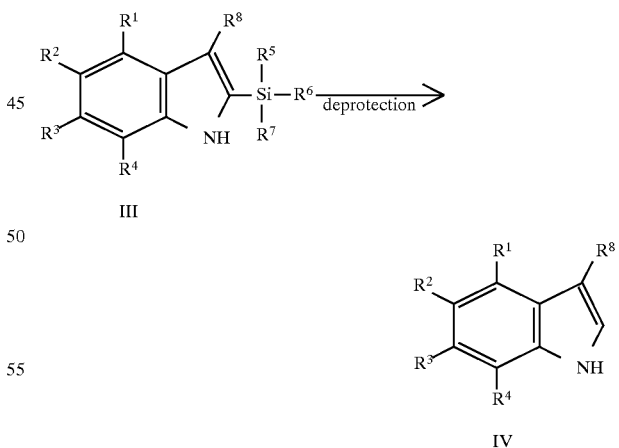

wherein $R^1$, $R^2$, $R^3$, $R^4$, $R^5$ $R^6$, $R^7$, and $R^8$ are as defined above.

The Si($R^5$)($R^6$)($R^7$) group is removable by Lewis acid catalyzed deprotection with a Lewis acid such as AlCl$_3$, or aqueous HCl HF, HBr, and HF. The silyl group may be removed, for example, by treatment with nucleophilic acid, e.g., contacting with about a 1:1 by volume 2N HCl/MeOH solvent mixture at 0°–30° C. for 1 to 24 hours to completely remove the silyl protecting groups. Alternatively, the silyl group may be removed by fluoride deprotection. This step is referred to herein as "deprotection". Removal of the Si($R^5$)($R^6$)($R^7$) group produces the 2-unsubstituted indole.

Particular 2-unsubstituted indole compounds according to structural formula (IV) that may be made according to the process of the present invention include:

(1) 1-benzyl-4-[3-(5-(1,2,4-triazol-4-yl)-1H-indol-3-yl)propyl]piperazin-2-one;
(2) 1-(2-phenylethyl)-4-[3-(5-(1,2,4-triazol-4-yl)-1H-indol-3-yl)propyl]piperazin-2-one;
(3) 1-[2-(3-fluorophenyl)ethyl]-4-[3-(5-(1,2,4-triazol-4-yl)-1H-indol-3-yl)propyl]piperazin-2-one;
(4) (3S)-3-(N-benzyl)aminomethyl-1-[2-(5-(N-methyl)-aminosulphonylmethyl)-1H-indol-3-yl)ethyl]pyrrolidine;
(5) (3S)-3-(N-benzyl)aminomethyl-1-[2-(5-(aminosulphonylmethyl)-1H-indol-3-yl)ethyl]pyrrolidine;
(6) (3S)-3-(N-benzyl)aminomethyl-(S)-1-[2-(5-(2-oxo-1,3-oxazolidin-4-ylmethyl)-1H-indol-3-yl)ethyl]pyrrolidine;
(7) (3S)-3-[N-(R)-α-(hydroxymethyl)benzyl]aminomethyl-(S)-1-[2-(5-(2-oxo-1,3-oxazolidin-4-ylmethyl)-1H-indol-3-yl)ethyl]pyrrolidine;
(8) (3S)-3-[N-(S)-α-methylbenzyl]aminomethyl-(S)-1-[2-(5-(2-oxo-1,3-oxazolidin-4-ylmethyl)-1H-indol-3-yl)ethyl]pyrrolidine;
(9) 4-[N-(R)-α-(hydroxymethyl)benzyl]amino-(S)-1-[3-(5-(2-oxo-1,3-oxazolidin-4-ylmethyl)-1H-indol-3-yl)propyl]piperidine;
(10) (3S)-3-(N-benzyl-N-methyl)aminomethyl-(S)-1-[2-(5-(3-methyl-2-oxo-1,3-oxazolidin-4-ylmethyl)-1H-indol-3-yl)ethyl]pyrrolidine;
(11) (3R)-3-[N-(S)-α-methylbenzyl-N-methyl]aminomethyl-(S)-1-[2-(5-(2-oxo-1,3-oxazolidin4-ylmethyl)-1H-indol-3-yl)ethyl]pyrrolidine;
(12) (3R)-3-[N-(S)-α-methylbenzyl-N-methyl]aminomethyl-(S)-1-[2-(5-(3-methyl-2-oxo-1,3-oxazolidin-4-ylmethyl)-1H-indol-3-yl)ethyl]pyrrolidine;
(13) (3S)-3-[N-(4-fluorobenzyl)-N-methyl]aminomethyl-(S)-1-[2-(5-(3-methyl-2-oxo-1,3-oxazolidin-4-ylmethyl)-1H-indol-3-yl)ethyl]pyrrolidine;
(14) 4-benzyl 12-[2-fluoromethyl-3-(5-(1,2,4-triazol-4-yl)-1H-indol-3-yl)propyl]piperazine;
(15) 4-[2-(3-fluorophenyl)ethyl]-1-[2-fluoro-3-(5-(1,2,4-triazol-4-yl)-1H-indol-3-yl)propyl]piperazine;
(16) 4-benzyl-1-[2-fluoro-3-(5-(1,2,4-triazol-4-yl)-1H-indol-3-yl)propyl]piperidine;
(17) 4-(N-benzyl-N-methylamino)-1-[2-fluoro-3-(5-(1,2,4-triazol-4-yl)-1H-indol-3-yl)propyl]piperidine;
(18) 4-[(R)-2-hydroxy-1-(4-fluorophenyl)ethylamino]-1-[2-fluoro-3-(5-(1,2,4-triazol-4-yl)-1H-indol-3-yl)propyl]piperidine;
(19) 7-benzyl-2-[2-(5-(1,2,4-triazol-4-yl)-1H-indol-3-yl)ethyl]-cis-2,7-diazabicyclo[3.3.0]octane;
(20) 7-(3-furylmethyl-2-[2-(5-(1,2,4-triazol-4-yl)-1H-indol-3-yl)ethyl]-cis-2,7-diazabicyclo[3.3.0]octane;
(21) 7-(2-phenylethyl)-2-[2-(5-(1,2,4-triazol-4-yl)-1H-indol-3-yl)ethyl]-cis-2,7-diazabicyclo[3.3.0]octane;
(22) 7-(4-fluorobenzyl-2-[2-(5-(1,2,4-triazol-4-yl)-1H-indol-3-yl)ethyl]-cis-2,7-diazabicyclo[3.3.0]octane;
(23) 7-(2,4-difluorobenzyl-2-[2-(5-(1,2,4-triazol-4-yl)-1H-indol-3-yl)ethyl]-cis-2,7-diazabicyclo[3.3.0]octane;
(24) 4-(2,2-difluoro-1-oxo-2-phenylethyl)-1-[3-(5-(1,2,4-triazol-4-yl)-1H-indol-3-yl)propyl]piperazine;
(25) 4-benzyl-3-methyl-1-[3-(5-(1,2,4-triazol-4-yl)-1H-indol-3-yl)propyl]-1,2,5,6-tetrahydropyridine;
(26) 4-benzyl-3-methoxymethyl-1-[3-(5-(1,2,4-triazol-4-yl)-1H-indol-3-yl)propyl]-1,2,5,6-tetrahydropyridine;
(27) 1-(2-hydroxy-1-phenylethyl)-4-[3-(5-(1,2,4-triazol-4-yl)-1H-indol-3-yl)propyl]piperidine;
(28) 1-[2-(2-fluorophenyl)ethyl]-4-[3-(5-(1,2,4-triazol-4-yl)-1H-indol-3-yl)propyl]piperidine;
(29) 1-benzyl-4-[3-(5-(1,2,4-triazol-4-yl)-1H-indol-3-yl)propyl]piperidine;
(30) 1-(3,3-dimethylbutyl)-4-[3-(5-(1,2,4-triazol-4-yl)-1H-indol-3-yl)propyl]piperidine;
(31) 1-(2-phenylethyl)-4-[3-(5-(1,2,4-triazol-4-yl)-1H-indol-3-yl)propyl]piperidine;
(32) 1-cyclohexylmethyl-4-[3-(5-(1,2,4-triazol-4-yl)-1H-indol-3-yl)propyl]piperidine;
(33) 1-(3-phenylpropyl)-4-[3-(5-(1,2,4-triazol-4-yl)-1H-indol-3-yl)propyl]piperidine;
(34) 1-[2-(3-fluorophenyl)ethyl]-4-[3-(5-(1,2,4-triazol-4-yl)-1H-indol-3-yl)propyl]piperidine;
(35) 1-[2-(4-trifluoromethylphenyl)ethyl]-4-[3-(5-(1,2,4-triazol-4-yl)-1H-indol-3-yl)propyl]piperidine;
(36) 1-[2-(3,4-difluorophenyl)ethyl]-4-[3-(5-(1,2,4-triazol-4-yl)-1H-indol-3-yl)propyl]piperidine;
(37) N-methyl-2-phenyl-2-[4-(3-(5-(1,2,4-triazol-4-yl)-1H-indol-3-yl)propyl)piperidin-1-yl]acetamide;
(38) 1-(2-oxo-2-phenylethyl)-4-[3-(5-(1,2,4-triazol-4-yl)-1H-indol-3-yl)propyl]piperidine;
(39) 1-(2-phenylpropyl)-4-[3-(5-(1,2,4-triazol-4-yl)-1H-indol-3-yl)propyl]piperidine;
(40) 4-benzyl-4-fluoro-1-[3-(5-(1,2,4-triazol-4-yl)-1H-indol-3- yl)propyl]piperidine;
(41) 4-fluoro-4-[2-(3-fluorophenyl)ethyl]-1-[3-(5-(1,2,4-triazol-4-yl)-1H-indol-3-yl)propyl]piperidine;
(42) 4-fluoro-4-(3-fluorobenzyl)-1-[3-(5-(1,2,4-triazol-4-yl)-1H-indol-3-yl)propyl]piperidine;
(43) 4-fluoro-4-(2-fluorobenzyl)-1-[3-(5-(1,2,4-triazol-4-yl)-1H-indol-3-yl)propyl]piperidine;
(44) 4-benzyl-4-methoxy-1-[3-(5-(1,2,4-triazol-4-yl)-1H-indol-3-yl)propyl]piperidine;
(45) 4-benzyl-4-methoxy-1-[3-(5-(1,2,4-triazol-1-ylmethyl)-1H-indol-3-yl)propyl]piperidine;
(46) 4-(2-fluorobenzyl)-4-methoxy-1-[3-(5-(1,2,4-triazol-4-yl)-1H-indol-3-yl)propyl]pipenidine;
(47) 4-(3-fluorobenzyl)-4-methoxy-1-[3-(5-(1,2,4-triazol-4-yl)-1H-indol-3-yl)propyl]piperidine;
(48) 4-(4-fluorobenzyl)-4-methoxy-1-[3-(5-(1,2,4-triazol-4-yl)-1H-indol-3-yl)propyl]piperidine;
(49) 1-[3-(5-(1,2,4-triazol-4-yl)-1H-indol-3-yl)propyl]-4-[2-(oxazole-2-on-3-yl)-1-phenylethyl]piperazine;
(50) 1-[3-(5-(1,2,4-triazol-4-yl)-1H-indol-3-yl)propyl]-4-[2-(oxazolidin-2-on-3-yl)-1-phenylethyl]piperazine;
(51) 1-[3-(5-(1,2,4-triazol-4-yl)-1H-indol-3-yl)propyl]-4-[1-(4-fluorophenyl)-2-(oxazolidin-2-on-3-yl)ethyl]piperazine;
(52) 1-[3-(5-(1,2,4-triazol-4-yl)-1H-indol-3-yl)propyl]-4-(3-hydroxy-1-phenylpropyl)piperazine;

(53) 1-[3-(5-(1,2,4-triazol-4-yl)-1H-indol-3-yl)propyl]-4-[2-(imidazole-1-yl)-1-phenylethyl]piperazine;
(54) 1-[3-(5-(1,2,4-triazol-4-yl)-1H-indol-3-yl)propyl]-4-[-(4-fluorophenyl)-2-hydroxyethyl]piperazine;
(55) 1-[3-(5-(1,2,4-triazol-4-yl)-1H-indol-3-yl)propyl]-4-[1-fluorophenyl)-2-methoxyethyl]piperazine;
(56) 1-[3-(5-(1,2,4-triazol-4-yl)-1H-indol-3-yl)propyl]-4-[3-(5-methyl-1,2,4-oxadiazol-3-yl)-1-phenylpropyl]piperazine; (57) 1-[3-(5-(1,2,4-triazol-4-yl)-1H-indol-3-yl)propyl]-4-[2-benzyloxy-1-(4-fluorophenyl)ethyl]piperazine;
(58) 1-[3-(5-(1,2,4-triazol-4-yl)-1H-indol-3-yl)propyl]-4-[1-(4-fluorophenyl)-3-methoxypropyl]piperazine;
(59) 1-[3-(5-(1,2,4-triazol-4-yl)-1H-indol-3-yl)propyl]-4-[1-fluorophenyl)-2-(imidazol-1-yl)ethyl]piperazine;
(60) 1-[3-(5-(1,2,4-triazol-4-yl)-1H-indol-3-yl)propyl]-4-[1-phenyl-2-(pyrrolidin-1-yl)ethyl]piperazine;
(61) 1-[3-(5-(1,2,4-triazol-4-yl)-1H-indol-3-yl)propyl]-4-[1-(4-fluorophenyl)-3-hydroxypropyl]piperazine;
(62) 1-[3-(5-(1,2,4-triazol-4-yl)-1H-indol-3-yl)propyl]-4-[3-(imidazol-1-yl)-1H-phenylpropyl]piperazine;
(63) 1-[3-(5-(1,2,4-triazol-4-yl)-1H-indol-3-yl)propyl]-4-(3-hydroxy-2-phenylpropyl)piperazine;
(64) 1-[3-(5-(1,2,4-triazol-4-yl)-1H-indol-3-yl)propyl]-4-(3-methoxy-2-phenylpropyl)piperazine;
(65) 1-[3-(5-(1,2,4-triazol-4-yl)-1H-indol-3-yl)propyl]-4-[2-(4-fluorophenyl)-3-hydroxypropyl]piperazine;
(66) 1-[3-(5-(1,2,4-triazol-4-yl)-1H-indol-3-yl)propyl]-4-[1-(4-fluorophenyl)prop-2-yl]piperazine;
(67) 1-[3-(5-(1,2,4-triazol-4-yl)-1H-indol-3-yl)propyl]-4-[2-(4-fluorophenyl)propyl]piperazine;
(68) 1-[3-(5-(1,2,4-triazol-4-yl)-1H-indol-3-yl)propyl]-4-[1-(4-fluorophenyl)-3-hydroxypropyl-2-yl]piperazine;
(69) 1-[3-(5-(1,2,4-triazol-4-yl)-1H-indol-3-yl)propyl]-4-[1-(4-fluorophenyl)-3-methoxyprop-2-yl]piperazine;
(70) 1-[3-(5-(1,2,4-triazol-4-yl)-1H-indol-3-yl)propyl]-4-[2-(3-fluorophenyl)-ethyl]piperazine;
(71) 1-[3-(5-(1,2,4-triazol-4-yl)-1H-indol-3-yl)propyl]-4-[2-(2-fluorophenyl)-ethyl]piperazine;
(72) 1-[3-(5-(1,2,4-triazol-4-yl)-1H-indol-3-yl)propyl]-4-[2-(4-fluorophenyl)-ethyl]piperazine;
(73) 1-[3-(5-(1,2,4-triazol-4-yl)-1H-indol-3-yl)propyl]-4-[2-(3-methoxyphenyl)-ethyl]piperazine;
(74) 1-[3-(5-(1,2,4-triazol-4-yl)-1H-indol-3-yl)propyl]-4-[2-(3-trifluoromethyl-phenyl)ethyl]piperazine;
(75) 1-[3-(5-(1,2,4-triazol-4-yl)-1H-indol-3-yl)propyl]-4-[2-(3,4-difluorophenyl)-ethyl]piperazine;
(76) 1-[3-(5-(1,2,4-triazol-4-yl)-1H-indol-3-yl)propyl]-4-[2-(2,4-difluorophenyl)-ethyl]piperazine;
(77) 1-[3-(5-(1,2,4-triazol-4-yl)-1H-indol-3-yl)propyl]-4-[2-(3,5-difluorophenyl)-ethyl]piperazine;
(78) 1-[3-(5-(1,2,4-triazol-4-yl)-1H-indol-3-yl)propyl]-4-[2-(3-(oxazolidin-2-on-3-yl)phenyl)ethyl]piperazine;
(79) N-methyl-3-[5-(1,2,4-triazol-4-yl)-1H-indol-3-yl]pyrrolidine;
(80) N-methyl-4-[5-(1,2,4-triazol-4-yl)-1 H-indol-3-yl]piperidine;
(81) N,N-dimethyl-2-[5-(1,2,4-triazol-4-yl)-1H-indol-3-yl]ethylamine;
(82) 4-(1-phenylethyl)-1-[3-(5-(1,2,4-triazol-4-yl)-1H-indol-3-yl)propyl]-1,2,5,6-tetrahydropyridine;
(83) 4-(ac-isopropyloxy)phenylmethyl-1-[3-(5-(1,2,4-triazol-4-yl)-1H-indol-3-yl)propyl]-1,2,5,6-tetrahydropyridine;
(84) 4-(a-methoxy)phenylmethyl-1-[3-(5-(1,2,4-triazol-4-yl)-1H-indol-3-yl)propyl]-1,2,5,6-tetrahydropyridine;
(85) 4-[c-(2-methoxyethyl)oxy]phenylmethyl-1-[3-(5-(1,2,4-triazol-4-yl)-1H-indol-3-yl)propyl]-1,2,5,6-tetrahydropyridine;
(86) 4-benzyl-1-[3-(2,3-dihydro-5-(1,2,4-triazol-4-yl)-1H-indol-3-yl)propyl]piperazine;
(87) 1-[3-(2,3-dihydro-5-(1,2,4-triazol-4-yl)-1H-indol-3-yl)propyl]-4-(pyridin-3-ylmethyl)piperazine;
(88) 1-[2-(5-(1,2,4-triazol-4-yl)-1H-indol-3-yl)propyl]-4-[2-(4-fluorophenyl)-4-methylpiperazin-1-yl]piperidine;
(89) 1-[2-(5-(1,2,4-triazol-1-ylmethyl)-1H-indol-3-yl)ethyl]-3(R)-(3(R)-phenylmorpholin-4-ylmethyl)pyrrolidine;
(90) 1-[3-(5-(1,2,4-triazol-4-yl)-1H-indol-3-yl)propyl]-4-(3-oxo-2-phenylpiperazin-1-yl)methylpiperidine;
(91) 1-[3-(5-(1,2,4-triazol-4-yl)-1H-indol-3-yl)propyl]-4-(4-methyl-2-phenylpiperazin-1-yl)piperidine;
(92) 1-[3-(5-(1,2,4-triazol-4-yl)-1H-indol-3-yl)propyl]-4-(benzimidazol-2-on-1-yl)piperidine;
(93) 1-[3-(5-(1,2,4-triazol-4-yl)-1H-indol-3-yl)propyl]-4-[6-(4-fluorophenyl)-4-methyl-3-oxopiperazin-1-yl]piperidine;
(94) [3-(3-(4-(2-(3,4-difluorophenyl)ethyl)piperazin-1-yl)propyl)-1H-indol-5-ylmethyl]oxazolidin-2-one;
(95) (S)-4-[3-(3-(4-(2-(3,4-difluorophenyl)ethyl)piperazin-1-yl)propyl)-1H-indol-5-ylmethyl]-3-methyloxazolidin-2-one;
(96) 1-[3-(5-(N-methylaminosulphonylmethyl)-1H-indol-3-yl)propyl]-4-[2-(4-(acetylamino)phenyl)ethyl]piperazine;
(97) 3-benzyl-7-[3-(5-(1,2,4-triazol-4-yl)-1H-indol-3-yl)propyl]-cis-3,7-diazabicyclo[3.3.0]octane;
(98) 3-(pyridin-3-yl)methyl-7-[3-(5-(1,2,4-triazol-4-yl)-1H-indol-3-yl)propyl]-cis-3,7-diazabicyclo[3.3.0]octane;
(99) 3-[2-(4-(acetylamino)phenyl)ethyl]-7-[3-(5-(1,2,4-triazol-4-yl)-1H-indol-3-yl)propyl]-cis-3,7-diazabicyclo[3.3.0]octane;
(100) 3-benzoyl-7-[3-(5-(1,2,4-triazol-4-yl)-1H-indol-3-yl)propyl]-cis-3,7-diazabicyclo[3.3.0]octane;
(101) (1RS,3RS,5RS)-7-benzyl-3-[5-(imidazol-1-yl)-1H-indol-3-ylmethyl]-2-methyl-2,7-diazabicyclo[3.3.0]octane;
(102) (1RS,3RS,5RS)-7-[2-(3-fluorophenyl)ethyl]-2-methyl-3-[5-(1,2,4-triazol-4-yl)-1H-indol-3-ylmethyl]-2,7-diazabicyclo[3.3.0]octane;
(103) (IRS,3RS,5RS)-7-(4-fluorobenzyl)-2-methyl-3-[5-(1,2,4-triazol-4-yl)-1H-indol-3-ylmethyl]-2,7-diazabicyclo[3.3.0]octane;
(104) 4-[1-(phenyl)-N,N-dimethylcarboxamidomethyl]-1-[3-(5-(1,2,4-triazol-4-yl)-1H-indol-3-yl)propyl]piperazine;
(105) 4-(2-methoxycarbonylamino-1-phenylethyl)-1-[3-(5-(1,2,4-triazol-4-yl)-1H-indol-3-yl)propyl]piperazine;
(106) 4-(2-dimethylamino-1-phenylethyl)-1-[3-(5-(1,2,4-triazol-4-yl)-1H-indol-3-yl)propyl]piperazine;
(107) 1-[3-(5-(1,2,4-triazol-4-yl)-1H-indol-3-yl)propyl]-4-(4-fluorophenyl)methylpiperazine;
(108) 4-[2-(N-methyl-N-methoxycarbonyl)amino-1-phenylethyl]-1-[3-(5-(1,2,4-triazol-4-yl)-1H-indol-3-yl)propyl]piperazine;

(109) 1-benzyl-4-[(R,S)-2-hydroxymethyl-3-(5-(1,2,4-triazol-4-yl)-1H-indol-3-yl)propyl]piperazine;
(110) 1-[3-(5-(1,2,4-triazol-4-yl)-1H-indol-3-yl)propyl]-4-[2-(1H-tetrazol-5-yl)phenyl]methylpiperazine;
(111) 1-[3-(5-(1,2,4-triazol-4-yl)-1H-indol-3-yl)propyl]-4-(2-phenylethyl)piperazine;
(112) 4-benzyl-1-[3-(5-(1,2,4-triazol-4-yl)-1H-indol-3-yl)propyl]piperazine;
(113) 4-[2-(2-methyltetrazol-5-yl)phenyl]methyl-1-[3-(5-(1,2,4-triazol-4-yl)-1H-indol-3-yl)propyl]piperazine;
(114) 4-[2-(1-methyltetrazol-5-yl)phenyl]methyl-1-[3-(5-(1,2,4-triazol-4-yl)-1H-indol-3-yl)propyl]piperazine;
(115) 4-[2-(N-methylcarboxamido)phenyl]methyl-1-[3-(5-(1,2,4-triazol-4-yl)-1H-indol-3-yl)propyl]piperazine;
(116) 4-[2-(N,N-dimethylaminomethyl)phenyl]methyl-1-[3-(5-(1,2,4-triazol-4-yl)-1H-indol-3-yl)propyl]piperazine;
(117) 4-(but-3-enyl)-1-[3-(5-(1,2,4-triazol-4-yl)-1H-indol-3-yl)propyl]piperazine;
(118) 4-(3-methylbutyl-2-enyl)-1-[3-(5-(1,2,4-triazol-4-yl)-1H-indol-3-yl)propyl]piperazine;
(119) 4-(prop-2-enyl)-1-[3-(5-(1,2,4-triazol-4-yl)-1H-indol-3-yl)propyl]piperazine;
(120) 4-(prop-2-ynyl)-1-[3-(5-(1,2,4-triazol-4-yl)-1H-indol-3-yl)propyl]piperazine;
(121) 4-[(R,S)-1-(phenyl)carboxamidomethyl]-1-[3-(5-(1,2,4-triazol-4-yl)-1H-indol-3-yl)propyl]piperazine;
(122) 4-[1-(phenyl)-N-methylcarboxamidomethyl]-1-[3-(5-(1,2,4-triazol-4-yl)-1H-indol-3-yl)propyl]piperazine;
(123) 1-[3-(5-(1,2,4-triazol-1-ylmethyl)-1H-indol-3-yl)propyl]-4-[2-(4-(acetylamino)phenyl)ethyl]piperazine;
(124) 1-[3-(5-(1,2,4-triazol-4-yl)-1H-indol-3-yl)propyl]-4-[2-(3-(acetylamino)phenyl)ethyl]piperazine;
(125) 1-[3-(5-(1,2,4-triazol-4-yl)-1H-indol-3-yl)propyl]-4-[4-(aminosulphonyl)phenyl]methylpiperazine;
(126) 1-[3-(5-(1,2,4-triazol-4-yl)-1H-indol-3-yl)propyl]-4-(furan-3-yl)methylpiperazine;
(127) 1-[3-(5-(1,2,4-triazol-4-yl)-1H-indol-3-yl)propyl]-4-(furan-2-yl)methylpiperazine;
(128) 1-[3-(5-(1,2,4-triazol-4-yl)-1H-indol-3-yl)propyl]-4-(thien-2-yl)methylpiperazine;
(129) 1-benzyl-4-[(R,S)-2-hydroxy-3-(5-(1,2,4-triazol-4-yl)-1H-indol-3-yl)propyl]piperazine;
(130) 1-[2-(4-(acetylamino)phenyl)ethyl]-4-[(R,S)-2-hydroxy-3-(5-(1,2,4-triazol-4-yl)-1H-indol-3-yl)propyl]piperazine;
(131) 1-[3-(5-(1,2,4-triazol-4-yl)-1H-indol-3-yl)propyl]-4-[2-(4-(aminocarbonylamino)phenyl)ethyl]piperazine;
(132) 1-[3-(5-(1,2,4-triazol-4-yl)-1H-indol-3-yl)propyl]-4-(4-cyanophenyl)methylpiperazine;
(133) 1-[3-(5-(1,2,4-triazol-4-yl)-1H-indol-3-yl)propyl]-4-[2-(4-cyanophenyl)ethyl]piperazine;
(134) 1-[3-(5-(1,2,4-triazol-4-yl)-1H-indol-3-yl)propyl]-4-[2-(4-(1,2,4-triazol-4-yl)phenyl)ethyl]piperazine;
(135) 1-[3-(5-(1,2,4-triazol-1-yl)-1H-indol-3-yl)propyl]-4-[2-(4-(acetylamino)phenyl)ethyl]piperazine;
(136) 1-[3-(5-(1,2,4-triazol-1-yl)-1H-indol-3-yl)propyl]-4-benzylpiperazine;
(137) 1-[3-(5-(1,2,4-triazol-1-ylmethyl)-1H-indol-3-yl)propyl]4-benzylpiperazine;
(138) 4-(4-acetylaminophenyl)methyl-1-[3-(5-(1,2,4-triazol-4-yl)-1H-indol-3-yl)propyl]piperidine;
(139) 4-benzyl-1-[3-(5-(1,2,4-triazol-4-yl)-1H-indol-3-yl)propyl]-1,2,5,6-tetrahydropyridine;
(140) 1-[3-(5-(1,2,4-triazol-4-yl)-1H-indol-3-yl)propyl]-4-(2-aminopyridin-5-yl)methylpiperazine;
(141) 1-[3-(5-(1,2,4-triazol-4-yl)-1H-indol-3-yl)propyl]-4-(4-aminophenyl )methylpiperazine;
(142) 1-[4-(5-(1,2,4-triazol-4-yl)-1H-indol-3-yl)butyl]-4-benzylpiperazine;
(143) 1-[4-(5-(1,2,4-triazol-4-yl)-1H-indol-3-yl)butyl]-4-(pyridin-2-yl)methylpiperazine;
(144) 1-[4-(5-(1,2,4-triazol-4-yl)-1H-indol-3-yl)butyl]-4-(pyridin-3-yl)methylpiperazine;
(145) 1-[3-(5-(1,2,4-triazol-4-yl)-1 H-indol-3-yl)propyl]-4-[2-(4-aminophenyl)ethyl]piperazine;
(146) 1-[3-(5-(1,2,4-triazol-4-yl)-1H-indol-3-yl)propyl]-4-[2-(4-(acetylamino)phenyl)ethyl]piperazine;
(147) 1-[3-(5-(1,2,4-triazol-4-yl)-1H-indol-3-yl)propyl]-4-(imidazol-2-yl)methylpiperazine;
(148) 1-[3-(5-(1,2,4-triazol-4-yl)-1H-indol-3-yl)propyl]-4-[3-(acetylamino)phenyl]methylpiperazine;
(149) 1-[3-(5-(1,2,4-triazol-4-yl)-1H-indol-3-yl)propyl]-4-[4-(acetylamino)phenyl]methylpiperazine;
(150) 1-[4-(5-(1,2,4-triazol-4-yl)-1H-indol-3-yl)butyl]-4-[4-(acetylamino)phenyl]methylpiperazine;
(151) 1-[3-(5-(1,2,4-triazol-4-yl)-1H-indol-3-yl)propyl]-4-(2-methoxyphenyl)methylpiperazine;
(152) 1-[3-(5-(1,2,4-triazol-4-yl)-1H-indol-3-yl)propyl]-4-benzylpiperazine;
(153) 1-[3-(5-(1,2,4-triazol-4-yl)-1H-indol-3-yl)propyl]-4-(pyridin-3-yl)methylpiperazine;
(154) 1-[3-(5-(1,2,4-triazol-4-yl)-1H-indol-3-yl)propyl]-4-(pyridin-2-yl)methylpiperazine;
(155) 1-[3-(5-(1,2,4-triazol-4-yl)-1H-indol-3-yl)propyl]-4-(pyridin-4-yl)methylpiperazine;
(156) (3R)-3-benzyloxymethyl-1-[2-(5-(1,2,4-triazol-4-yl)-1H-indol-3-yl)ethyl]pyrrolidine;
(157) (3S)-3-(N-benzyl-N-methyl)aminomethyl 1-l[2-(5-(1,2,4-triazol-4-yl)-1H-indol-3-yl)ethyl]pyrrolidine;
(158) (2S)-2-(N-benzyl-N-methyl)aminomethyl-1-[2-(5-(1,2,4-triazol-4-yl)-1H-indol-3-yl)ethyl]pyrrolidine;
(159) (3S)-3-(N-benzyl)aminomethyl-1-[2-(5-(1,2,4-triazol-4-yl)-1H-indol-3-yl)ethyl]pyrrolidine;
(160) 4-(4-acetylaminophenyl)methylamino-1-[3-(5-(1,2,4-triazol-4-yl)-1H-indol-3-yl)propyl]piperidine;
(161) 1-[3-(5-(imidazol-1-yl)-1H-indol-3-yl)propyl]-4-[(R)-α-(methoxymethyl)benzylamino]piperidine;
(162) 1-[3-(5-(1,2,4-triazol-1-ylmethyl)-1H-indol-3-yl)propyl]-4-[(R)-1-(4-fluorophenyl)-2-methoxyethylamino]piperidine;
(163) 1-[3-(5-(1,2,4-triazol-1-ylmethyl)-1H-indol-3-yl)propyl]-4-[N-(4-fluorobenzyl)-N-methylamino]piperidine;
(164) 1-[3-(5-(1,2,4-triazol-4-yl)-1H-indol-3-yl)propyl]-4-(2-phenylpiperidin-1-yl)piperidine;
(165) 1-[3-(5-(1,2,4-triazol-4-yl)-1H-indol-3-yl)propyl]-4-[(R)-1-(4-fluorophenyl)-2-methoxyethylamino]piperidine;
(166) 1-[3-(5-(1,2,4-triazol-4-yl)-1H-indol-3-yl)propyl]-4-(indan-1-ylaminomethyl)piperidine;
(167) 1-[3-(5-(1,2,4-triazol-4-yl)-1H-indol-3-yl)propyl]-4-[N-(R)-α-(hydroxymethyl)benzyl-N-methylaminomethyl]-piperidine;

(168) (3R)-3-(benzylthio)methyl-1-[2-(5-(1,2,4-triazol-4-yl)-1H-indol-3-yl)ethyl]pyrrolidine;

(169) (±)-1-[3-(5-(1,2,4-triazol-4-yl)-1H-indol-3-yl)propyl]-4-(1-benzylamino-2-hydroxyethyl)piperidine;

(170) 1-[3-(5-(1,2,4-triazol-1-yl)-1H-indol-3-yl)propyl]-4-[(R)-α-(hydroxymethyl)benzylamino]piperidine;

(171) 1-[3-(5-(imidazol-1-yl)-1H-indol-3-yl)propyl]-4-[(R)-α-(methyl)benzylamino]piperidine;

(172) 1-[3-(5-(imidazol-1-yl)-1H-indol-3-yl)propyl]-4-[(R)-α-(hydroxymethyl)benzylamino]piperidine;

(173) 1-[3-(5-(1,2,4-triazol-1-ylmethyl)-1H-indol-3-yl)propyl]-4-[(R)-α-(hydroxymethyl)benzylamino]piperidine;

(174) 1-[3-(5-(1,2,4-triazol-4-yl)-1H-indol-3-yl)propyl]-4-[(R)-α-(methoxymethyl)benzylamino]piperidine;

(175) 1-[3-(5-(1,2,4-triazol-4-yl)-1H-indol-3-yl)propyl]-4-[N-(R)-α-(methoxymethyl)benzyl-N-methylamino]piperidine;

(176) (3R)-3-benzyloxy-1-[2-(5-(1,2,4-triazol-4-yl)-1H-indol-3-yl)ethyl]pyrrolidine;

(177) (3R)-3-(4-methoxyphenyl)methoxy-1-[2-(5-(1,2,4-triazol-4-yl)-1H-indol-3-yl)ethyl]pyrrolidine;

(178) (3R)-3-(pyridin-3-yl)methoxy-1-[2-(5-(1,2,4-triazol-4-yl)-1H-indol-3-yl)ethyl]pyrrolidine;

(179) (3R)-3-benzyloxymethyl-1-[2-(5-(1,2,4-triazol-4-yl)-1H-indol-3-yl)ethyl]pyrrolidine;

(180) (3S)-3-(N-benzyl-N-methyl)aminomethyl1-[2-(5-(1,2,4-triazol-4-yl)-1H-indol-3-yl)ethyl]pyrrolidine;

(181) (2S)-2-(N-benzyl-N-methyl)aminomethyl1-l[2-(5-(1,2,4-triazol-4-yl)-1H-indol-3-yl)ethyl]pyrrolidine;

(182) (3S)-3-(N-benzyl)aminomethyl-1-[2-(5-(1,2,4-triazol-4-yl)-1H-indol-3-yl)ethyl]pyrrolidine;

(183) 4-(4-acetylaminophenyl)methylamino-1-[3-(5-(1,2,4-triazol-4-yl)-1H-indol-3-yl)propyl]piperidine;

(184) 4-benzylamino-1-[3-(5-(1,2,4-triazol-4-yl)-1H-indol-3-yl)propyl]piperidine;

(185) 4-(N-benzyl-N-methyl)amino-1-[3-(5-(1,2,4-triazol-4-yl)-1H-indol-3-yl)propyl]piperidine;

(186) 4-(N-benzyl-N-methyl)aminomethyl-1-[3-(5-(1,2,4-triazol-4-yl)-1H-indol-3-yl)propyl]piperidine;

(187) 1-[3-(5-(1,2,4-triazol-4-yl)-1H-indol-3-yl)propyl]-4-[α-(methyl)benzylamino]piperidine;

(188) 1-[3-(5-(1,2,4-triazol-4-yl)-1H-indol-3-yl)propyl]-4-[α-(hydroxymethyl)benzylamino]piperidine;

(189) 1-[3-(5-(1,2,4-triazol-4-yl)-1H-indol-3-yl)propyl]-4-[(1-hydroxymethyl-2-phenyl)ethylamino]piperidine;

(190) 4-(N-benzyl)aminomethyl-1-[3-(5-(1,2,4-triazol-4-yl)-1H-indol-3-yl)propyl]piperidine;

(191) 1-[3-(5-(1,2,4-triazol-4-yl)-1H-indol-3-yl)propyl]-4-[(2-hydroxy-1-methyl-2-phenyl)ethylamino]piperidine;

(192) 1-[3-(5-(1,2,4-triazol-4-yl)-1H-indol-3-yl)propyl]-4-[2-(4-acetylaminophenyl)ethylamino]piperidine;

(193) 1-[3-(5-(1,2,4-triazol-4-yl)-1H-indol-3-yl)propyl]-4-[α-(methyl)benzylamino]methylpiperidine;

(194) 1-[3-(5-(1,2,4-triazol-4-yl)-1H-indol-3-yl)propyl]-4-[1-(4-acetylaminophenyl)ethylamino]methylpiperidine;

(195) 1-[3-(5-(1,2,4-triazol-4-yl)-1H-indol-3-yl)propyl]-4-[N-[α-(hydroxymethyl)benzyl]-N-methylamino]piperidine;

(196) 1-[3-(5-(1,2,4-triazol-4-yl)-1H-indol-3-yl)propyl]-4-[N-(2-(4-acetylaminophenyl)ethyl)-N-methylamino]piperidine;

(197) 1-[3-(5-(1,2,4-triazol-4-yl)-1H-indol-3-yl)propyl]-4-[N-(4-acetylaminobenzyl)-N-methylamino]methylpiperidine;

(198) 1-[3-(5-(1,2,4-triazol-4-yl)-1H-indol-3-yl)propyl]-4-[N-(thien-2-yl)methyl-N-methylamino]piperidine;

(199) 1-[3-(5-(1,2,4-triazol-4-yl)-1H-indol-3-yl)propyl]-4-[(R)-α-(hydroxymethyl)benzylamino]methylpiperidine;

(200) 3-(4-acetylaminobenzyl)aminomethyl-1-[2-(5-(1,2,4-triazol-4-yl)-1H-indol-3-yl)ethyl]pyrrolidine;

(201) (3R)-3-(N-benzyl)aminomethyl-1-[2-(5-(1,2,4-triazol-4-yl)-1H-indol-3-yl)ethyl]pyrrolidine;

(202) (3S)-3-(pyridin-4-ylmethyl)aminomethyl-1-[2-(5-(1,2,4-triazol-4-yl)-1H-indol-3-yl)ethyl]pyrrolidine;

(203) 3-(N-benzyl)aminomethyl-1-[2-(5-(1,2,4-triazol-4-yl)-1H-indol-3-yl)ethyl]azetidine;

(204) 4-benzyl-4-hydroxy-1-[3-(5-(1,2,4-triazol-4-yl)-1H-indol-3-yl)propyl]piperidine;

(205) 3-(N-benzyl)aminomethyl-1-[3-(5-(1,2,4-triazol-4-yl)-1H-indol-3-yl)propyl]azetidine;

(206) 4-(N-benzyl)aminomethyl-4-hydroxy-1-[3-(5-(1,2,4-triazol-4-yl)-1H-indol-3-yl)propyl]piperidine;

(207) 4-(N-benzyl-N-methyl)aminomethyl-4-hydroxy-1-[3-(5-(1,2,4-triazol-4-yl)-1H-indol-3-yl)propyl]piperidine;

(208) 3-(N-benzyl-N-methyl)aminomethyl-1-[2-(5-(1,2,4-triazol-4-yl)-1H-indol-3-yl)ethyl]azetidine;

(209) (3S)-3-[N-α-(methyl)benzyl]aminomethyl-1-[2-(5-(1,2,4-triazol-4-yl)-1H-indol-3-yl)ethyl]pyrrolidine;

(210) (3S)-3-[N-(furan-3-ylmethyl)amino]methyl-1-[2-(5-(1,2,4-triazol-4-yl)-1H-indol-3-yl)ethyl]pyrrolidine;

(211) (3S)-3-[N-(furan-2-ylmethyl)amino]methyl-1-[2-(5-(1,2,4-triazol-4-yl)-1H-indol-3-yl)ethyl]pyrrolidine;

(212) (3S)-3-[N-α-(hydroxymethyl)benzyl]aminomethyl-1-[2-(5-(1,2,4-triazol-4-yl)-1H-indol-3-yl)ethyl]pyrrolidine;

(213) (3S)-3-[N-benzyl-N-(2-hydroxy)ethyl]aminomethyl-1-[2-(5-(1,2,4-triazol-4-yl)-1H-indol-3-yl)ethyl]pyrrolidine;

(214) (3S)-3-[N-(2-phenylethyl)amino]methyl-1-[2-(5-(1,2,4-triazol-4-yl)-1H-indol-3-yl)ethyl]pyrrolidine;

(215) (3S)-3-[N-(2-phenylethyl)-N-methylamino]methyl-1-[2-(5-(1,2,4-triazol-4-yl)-1H-indol-3-yl)ethyl]pyrrolidine;

(216) (3S)-3-(N-α-dimethylbenzyl)aminomethyl-1-[2-(5-(1,2,4-triazol-4-yl)-1H-indol-3-yl)ethyl]pyrrolidine;

(217) (3S)-3-[N-(S)-α-methylbenzyl]aminomethyl-1-[2-(5-(1,2,4-triazol-1-yl)-1H-indol-3-yl)ethyl]pyrrolidine;

(218) (3S)-3-[N-(R)-α-(hydroxymethyl)benzyl]aminomethyl-1-[2-(5-(1,2,4-triazol-1-yl)-1H-indol-3-yl)ethyl]pyrrolidine;

(219) (3S)-3-(N-benzyl)aminomethyl-1-[2-(5-(1,2,4-triazol-1-ylmethyl)-1H-indol-3-yl)ethyl]pyrrolidine;

(220) (3S)-3-[N-(S)-α-methylbenzyl]aminomethyl-1-[2-(5-(1,2,4-triazol-1-ylmethyl)-1H-indol-3-yl)ethyl]pyrrolidine;

(221) (3S)-3-[N-(R)-α-(hydroxymethyl)benzyl]aminomethyl-1-[2-(5-(1,2,4-triazol-1-ylmethyl)-1H-indol-3-yl)ethyl]-pyrrolidine;

(222) (3S)-3-(N-benzyl-N-methyl)aminomethyl-1-[2-(5-(imidazol-1-yl)-1H-indol-3-yl)ethyl]pyrrolidine;

(223) (3S)-3-(N-benzyl-N-methyl)aminomethyl-1-[2-(5-(1,2,4-triazol-1-ylmethyl)-1H-indol-3-yl)ethyl]pyrrolidine;

(224) (3R)-3-[N-methyl-N-(S)-α-methylbenzyl]aminomethyl-1-[2-(5-(1,2,4-triazol-1-ylmethyl)-1H-indol-3-yl)ethyl]-pyrrolidine;
(225) (3R)-3-[N-methyl-N-(R)-α-hydroxymethylbenzyl]amino-methyl-1-[2-(5-(1,2,4-triazol-1-ylmethyl)-1H-indol-3-yl)ethyl]pyrrolidine;
(226) (3R)-3-[N-methyl-N-(S)-α-methylcyclohexylmethyl]amino-methyl-1-[2-(5-(1,2,4-triazol-1-ylmethyl)-1H-indol-3-yl)ethyl]pyrrolidine;
(227) (3R)-3-[3-(R)-hydroxy-2-(R)-phenylpiperidin-1-yl]methyl-1-[2-(5-(1,2,4-triazol-1-ylmethyl)-1H-indol-3-yl)ethyl]-pyrrolidine;
(228) (3R)-3-[3-(R)-hydroxy-2-(R)-phenylpiperidin-1-yl]methyl-1-[2-(5-(1,2,4-triazol-1-yl)-1H-indol-3-yl)ethyl]pyrrolidine;
(229) 4-hydroxy-4-(phenylsulfinyl)methyl-1-[3-(5-(1,2,4-triazol-4-yl)-1H-indol-3-yl)propyl]piperidine;
(230) (3R)-3-[2-(R,S)-phenylpiperidin-1-yl]methyl-1-[2-(5-(1,2,4-triazol-1-ylmethyl)-1H-indol-3-yl)ethyl]pyrrolidine;
(231) 4-(3,3-dimethylpiperidin-1-yl)methyl-4-hydroxy-1-[3-(5-(1,2,4-triazol-4-yl)-1H-indol-3-yl)propyl]piperidine;
(232) 4-hydroxy-4-(1,2,3,4-tetrahydroisoquinolin-2-yl)methyl-1-[3-(5-(1,2,4-triazol -4-yl)-1H-indol-3-yl)propyl]piperidine;
(233) 4-hydroxy-4-(N-isobutyl-N-methyl)aminomethyl-1-[3-(5-(1,2,4-triazol-4-yl)-1H-indol-3-yl)propyl]piperidine;
(234) 4-[N-benzyl-N-(2-hydroxyethyl)amino]methyl-4-hydroxy-1-[3-(5-(1,2,4-triazol-4-yl)-1H-indol-3-yl)propyl]-piperidine;
(235) 4-[N-(2,2-dimethylpropyl)-N-methylamino]methyl-4-hydroxy-1-[3-(5-(1,2,4-triazol-4-yl)-1H-indol-3-yl)propyl]piperidine;
(236) 4-[N-(R)-α-hydroxymethylbenzyl-N-methylamino]methyl-4-hydroxy-1-[3-(5-(1,2,4-triazol-4-yl)-1H-indol-3-yl)propyl]piperidine;
(237) 4-hydroxy-4-(2-pyridylmethyl)aminomethyl-1-[3-(5-(1,2,4-triazol-4-yl)-1H-indol-3-yl)propyl]piperidine;
(238) 4-hydroxy-4-(2-methylphenylmethyl)aminomethyl-1-[3-(5-(1,2,4-triazol-4-yl)-1H-indol-3-yl)propyl]piperidine;
(239) 4-hydroxy-4-[N-(2-methylphenylmethyl)-N-methylamino]methyl-1-[3-(5-(1,2,4-triazol-4-yl)-1H-indol-3-yl)propyl]piperidine;
(240) 3-(benzylamino)methyl-3-hydroxy-1-[3-(5-(1,2,4-triazol-4-yl)-1H-indol-3-yl)propyl]pyrrolidine;
(241) 3-(benzylamino)methyl-3-hydroxy-1-[2-(5-(1,2,4-triazol-4-yl)-1H-indol-3-yl)ethyl]pyrrolidine;
(242) 1-[3-(5-(1,2,4-triazol-4-yl)-1H-indol-3-yl)propyl]-4-[(R)-α-(carbamoyl-oxymethyl)benzylamino]piperidine;
(243) 1-[3-(5-(1,2,4-triazol-4-yl)-1H-indol-3-yl)propyl]-4-[(1R,2S)-2-hydroxy-1-phenylpropylamino]piperidine;
(244) 1-[3-(5-(1,2,4-triazol-4-yl)-1H-indol-3-yl)propyl]-4-[(1,2R)-2-hydroxy-1-phenylpropylamino]piperidine;
(245) 1-[3-(5-(1,2,4-triazol-4-yl)-1H-indol-3-yl)propyl]-4-[(R,S)-1-hydroxy-2-phenylprop-2-ylamino]piperidine;
(246) 1-[3-(5-(1,2,4-triazol-4-yl)-1H-indol-3-yl)propyl]-4-[(R)-2-hydroxy-1-(4-fluorophenyl)ethylamino]piperidine;
(247) 1-[3-(5-(1,2,4-triazol-4-yl)-1H-indol-3-yl)propyl]-4-[(1R ,2R)-2-hydroxyindan-1-ylamino)piperidine;
(248) 1-[3-(5-(1,2,4-triazol-4-yl)-1H-indol-3-yl)propyl]-4-[(R,S)-indan-1-ylamino]piperidine;
(249) 1-[3-(5-(1,2,4-triazol-4-yl)-1H-indol-3-yl)propyl]-4-[(R,S)-1-(4-fluorophenyl)ethylamino]piperidine;
(250) 1-[3-(5-(1,2,4-triazol-4-yl)-1H-indol-3-yl)propyl]-4-[(R)-1-phenylprop-2-ylamino]piperidine;
(251) 1-[3-(5-(1,2,4-triazol-4-yl)-1H-indol-3-yl)propyl]-4-[N-(thien-3-ylmethyl)-N-methylamino]piperidine;
(252) 1-[3-(5-(1,2,4-triazol-4-yl)-1H-indol-3-yl)propyl]-4-[N-(furan-3-ylmethyl)-N-methylamino]piperidine;
(253) 1-[3-(5-(1,2,4-triazol-4-yl)-1H-indol-3-yl)propyl]-4-(furan-3-ylmethyl)aminopiperidine;
(254) 1-[3-(5-(1,2,4-triazol-4-yl)-1H-indol-3-yl)propyl]-4-[N,N-di-(furan-3-ylmethyl)amino]piperidine;
(255) 1-[3-(5-(1,2,4-triazol-4-yl)-1H-indol-3-yl)propyl]-4-[N-(3,3-dimethylallyl)-N-methylamino]piperidine;
(256) 1-[3-(5-(1,2,4-triazol-4-yl)-1H-indol-3-yl)propyl]-4-(N-allyl-N-methylamino)piperidine;
(257) N,N-Dimethyl-2-[5-(1,2,4-triazol-1-ylmethyl)-1H-indol-3-yl]ethylamine;
(258) N,N-Dimethyl-2-[5-(1,3-imidazol-1-ylmethyl)-1H-indol-3-yl]ethylamine;
(259) N,N-Dimethyl-2-[5-(5-methyl-1,2,3,4-triazol-1-ylmethyl)-1H-indol-3-yl]ethylamine;
(260) N,N-Dimethyl-2-[5-(1,3,4-triazol-1-ylmethyl)-1H-indol-3-yl]ethylamine;
(261) N,N-Dimethyl-2-[5-(1,3,4-triazol-1-yl)-1H-indol-3-yl]ethylamine;
(262) N,N-Diethyl-2-[5-(1,2,4-triazol-1-ylmethyl)-1H-indol-3-yl]ethylamine;
(263) N,N-Diethyl-2-[5-(1,3-imidazol-1-ylmethyl)-1H-indol-3-yl]ethylamine;
(264) N,N-Diethyl-2-[5-(5-methyl-1,2,3,4-tetrazol-1-ylmethyl)-1H-indol-3-yl]ethylamine;
(265) N,N-Diethyl-2-[5-(1,3,4-triazol-1-ylmethyl)-1H-indol-3-yl]ethylamine;
(266) N,N-Diethyl-2-[5-(1,3,4-triazol-1-yl)-1H-indol-3-yl]ethylamine;
(267) N,N-Dimethyl-[5-(1,2,4-triazol-1-ylmethyl)-1H-indol-3-yl]methylamine;
(268) N,N-Dimethyl-[5-(1,3-imidazol-1-ylmethyl)-1H-indol-3-yl]methylamine;
(269) N,N-Dimethyl-[5-(5-methyl-1,2,3,4-tetrazol-1-ylmethyl)-1H-indol-3-yl]methylamine;
(270) N,N-Dimethyl-[5-(1,3,4-triazol-1-ylmethyl)-1H-indol-3-yl]methylamine;
(271) N,N-Dimethyl-[5-(1,3,4-triazol-1-yl)-1H-indol-3-yl]methylamine;
(272) N,N-Diethyl-3-[5-(1,2,4-triazol-1-ylmethyl)-1H-indol-3-yl]propylamine;
(273) N,N-Dimethyl-3-[5-(1,3-imidazol-1-yl)-1H-indol-3-yl]propylamine;
(274) N,N-Diethyl-3-[5-(5-methyl-1,2,3,4-tetrazol-1-ylmethyl)-1H-indol-3-yl]propylamine;
(275) N,N-Dimethyl-3-[5-(1,3,4-triazol-1-ylmethyl)-1H-indol-3-yl]propyl-amine;
(276) N,N-Diethyl-3-[5-(1,3,4-triazol-1-yl)-1H-indol-3-yl]propylamine;
(277) N,N-Dimethyl-4-[5-(3-methyl-1,2,4,5-tetrazol-1-ylmethyl)-1H-indol-3-yl]butylamine;

(278) N,N-Dimethyl-4-[5-(2-ethyl-1,3-ethyl-imidazol-1-ylmethyl)-1H-indol-3-yl]butylamine;

(279) N,N-Dimethyl-4-[5-(5-ethyl-1,2,3,4-triazol-1-ylmethyl)-1-indol-3-yl]butylamine;

(280) N,N-Dimethyl-4-[5-(2-methyl-1,3,4-triazol-1-ylmethyl) 1H-indol-3-yl]butylamine;

(281) N,N-Dimethyl-4-[5-(2-ethyl-1,3,4-triazol-1-yl)-1H-indol-3-yl]butylamine;

(282) 2-[5-(1,2,4-triazol-1-ylmethyl)-1H-indol-3-yl]ethylalcohol;

(283) 2-[5-(1,3-imidazol-1-ylmethyl)-1H-indol-3-yl]ethylalcohol;

(284) 2-[5-(5-methyl-1,2,3,4-tetrazol-1-ylmethyl)-1H-indol-3-yl]ethylalcohol;

(285) 2-[5-(1,3,4-triazol-1-ylmethyl)-1H-indol-3-yl]ethylalcohol;

(286) 2-[5-(1,3,4-triazol-1-yl)-1H-indol-3-yl]ethylalcohol;

(287) [5-(1,2,4-triazol-1-ylmethyl)-1H-indol-3-yl]-methylalcohol;

(288) 3-[5-(1,3-imidazol-1-ylmethyl)-1H-indol-3-yl]propylalcohol;

(289) 4-[5-(5-methyl-1,2,3,4-tetrazol-1-ylmethyl)-1H-indol-3-yl]butylalcohol;

(290) 2-[5-(2-methyl-1,3,4-triazol-1-ylmethyl)-1H-indol-3-yl]ethylalcohol; and (291) 2-[5-(5-methyl-1,3,4-triazol-1-yl)-1H-indol-3-yl]ethylalcohol.

Further 2-unsubstituted indoles which may be made according to the process of the present invention include:

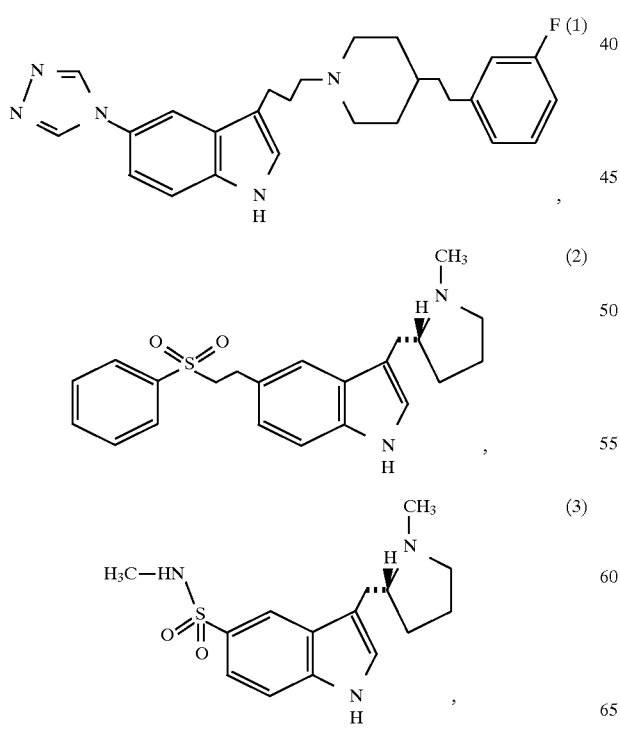

Preferred compounds that may be prepared according to the process of the present invention include:

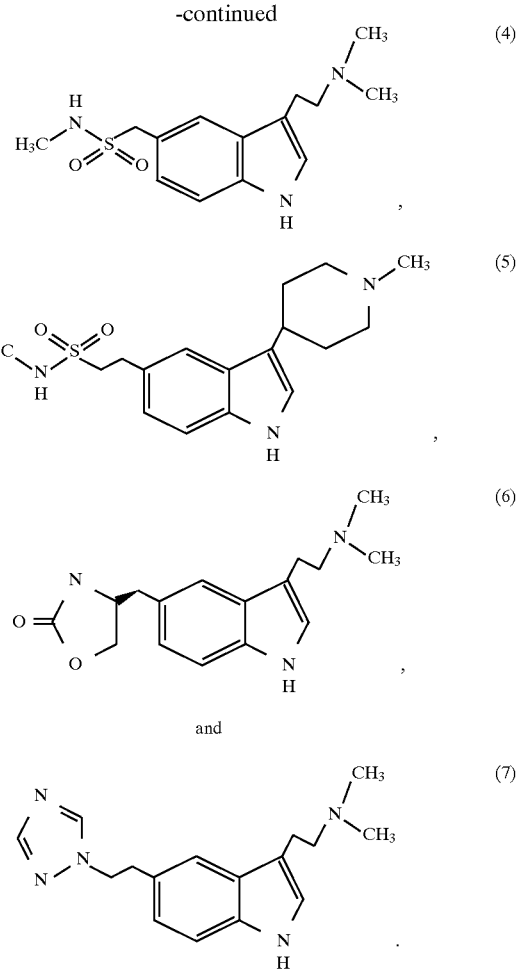

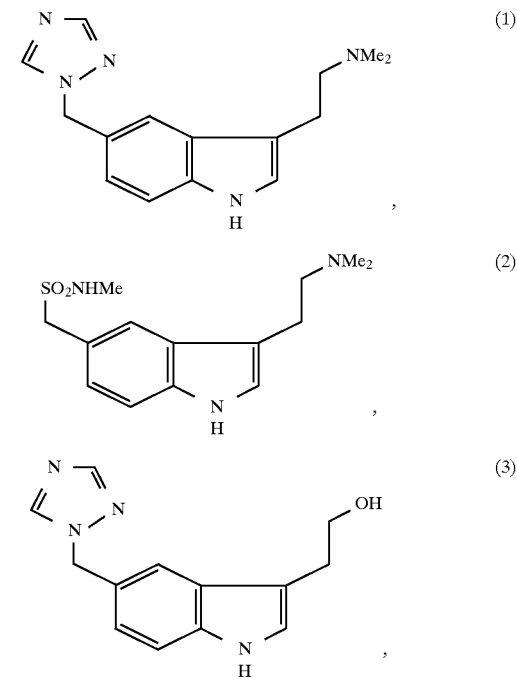

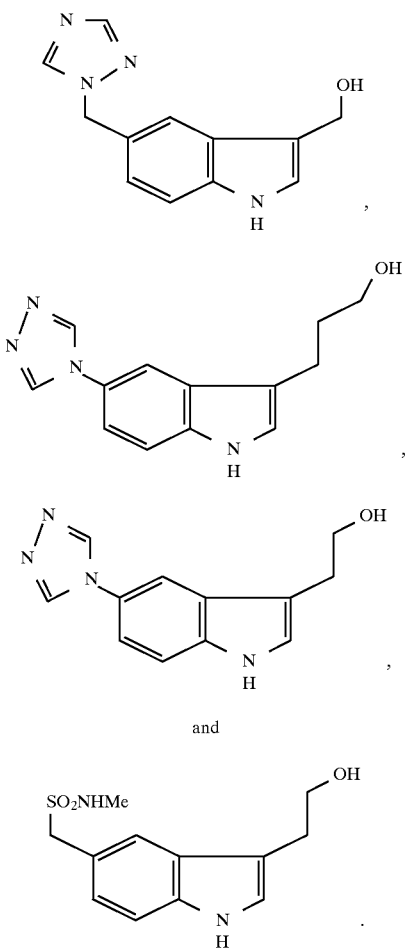

Still further, the present invention is also directed to the novel intermediates of structural formulae (V) and (VI).

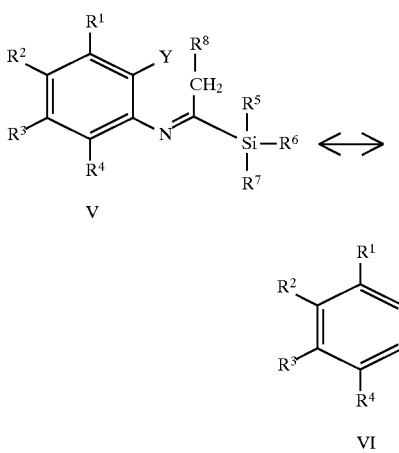

wherein Y, $R^1$, $R^2$, $R^3$, $R^4$, $R^5$, $R^6$, $R^7$, and $R^8$ are as defined above.

The acyl silanes employed in the present invention may be generally prepared according to the scheme below:

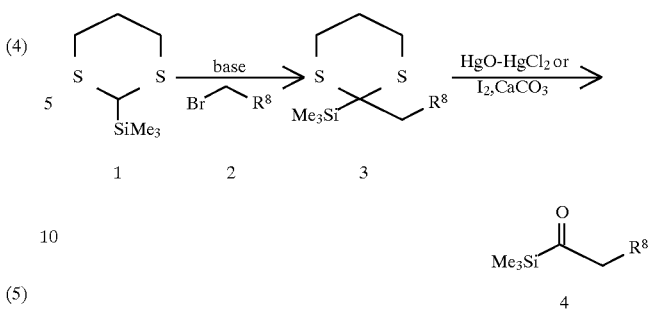

To TMS dithiane 1 in dry, polar aprotic solvent, such as THF, diethylether, t-butylmethylether, dioxane, diethoxymethane, is added an equivalent of a base such as lithium diisopropyl amide, NaH, Grignard, or an alkyl lithium, such as n-butyl lithium dropwise. Preferably, this alkylation is conducted at reduced temperatures, most preferably at −78° C. Following the addition, the mixture is preferably warmed to −20° C. and aged at −20° C. for 0.5 h. Following aging, the reaction is preferably cooled to −78° C. Br—$CH_2$—$R^8$ 2, preferably dissolved in a small volume of the solvent, is added dropwise. The mixture is warmed, preferably to room temperature, and aged, preferably for about 12 hours. The mixture is partitioned between a lipophilic solvent, such as heptane, and water. The heptane layer is separated and concentrated in vacuum to give the dithiane 3 as a pale yellow oil. This material may be directly used in the next step.

A mixture of the dithiane 3, mercuric oxide and mercuric chloride in acetonitrile-$H_2O$, (preferably an 80:20 ratio) in an aprotic solvent such as ethyl acetate, isopropyl acetate, methylene chloride, acetonitrile, toluene and the like, is aged at room temperature, preferably for about 30 minutes. Alternatively, iodine in calcium carbonate may be employed. The resulting solid is filtered and washed, preferably with an aprotic solvent such as ethyl acetate, isopropyl acetate, methylene chloride, acetonitrile, toluene and the like. The filtrate and wash are combined and concentrated to an oil. This material may be chromatographed over silica gel to give the acyl silane 4 as a pale yellow oil.

Additional syntheses of acyl silanes which may be used to prepare starting materials for the compounds of the present invention are described in the following references:

(1) Ricci et al., Synthesis 1989, pp. 647–660.
(2) Page et al., Chem. Soc. Rev. 1990, vol. 19, pp. 147–195.
(3) Cirillo et al., Org. Prep. Proc. Int. 1992, vol. 24, pp. 555–582.
(4) Plantier-Royon and Portella, Tetrahedron Letters 1996, vol. 37 (34), pp. 6113–6114.

The following examples are not intended to be limitations on the scope of the instant invention in any way, and they should not be so construed. Furthermore, the compounds described in the following examples are not to be construed as forming the only genus that is considered as the invention, and any combination of the compounds or their moieties may itself form a genus. Those skilled in the art will readily understand that known variations of the conditions and processes of the following preparative procedures can be used to prepare these compounds.

EXAMPLES

Example 1
Preparation of 2-trimethylsilyl indole

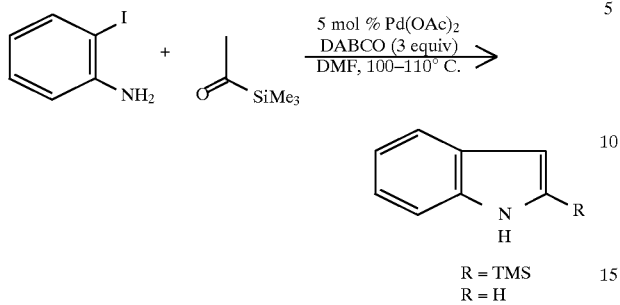

R = TMS
R = H

A mixture of iodoaniline (2.19 g, 10 mmol), acyl silane (2.36 g, 20 mmol, prepared according to the procedures of reference example A), DABCO (1,4-diazabicyclo[2.2.2]octane, 3.36 g, 30 mmol) and Pd(OAC)$_2$ (112.25 mg, 0.5 mmol) in 30 mL DMF was degassed via N$_2$/vacuum and heated at 105° C. for 36 h. The mixture was cooled to room temperature, diluted with IPAc (isopropyl acetate, 100 mL) and washed with 2×50 mL of water. The IPAc layer was concentrated in vacuum and chromatographed over silica gel to give 2-trimethylsilyl indole and indole.

Examples 2 to 8

According to the procedures of Example 2, starting with the appropriately substituted 2-iodo aniline, and the appropriate acyl silane, the following compounds are prepared:

| Example | Aniline | Acyl silane | Product |
|---|---|---|---|
| 6 | [triazolyl-phenyl with I and NH₂] | HO-(CH₂)₃-C(=O)-SiMe₃ | [triazolyl-indole with 3-(3-hydroxypropyl), 2-SiMe₃] |
| 7 | [triazolyl-phenyl with I and NH₂] | R¹⁷O-(CH₂)₂-C(=O)-SiMe₃ | [triazolyl-indole with 3-(2-OR¹⁷-ethyl), 2-SiMe₃] |
| 8 | MeHNO₂S-CH₂-[phenyl with I and NH₂] | R¹⁷O-(CH₂)₂-C(=O)-SiMe₃ | MeHNO₂S-CH₂-[indole with 3-(2-OR¹⁷-ethyl), 2-SiMe₃] | wherein $R^{17}$ is a hydroxy protecting group that is removable under mild acid hydrolysis.

Example 9

Preparation of Indole

A mixture of the 2-trimethylsilyl indole product of Example 1 (0.50 g, 2.6 mmol) in 5 mL methanol was treated with 2.5N HCl (2.11 mL, 5.2 mmol) and the reaction mixture was aged at room temperature for 2 h. Isopropyl acetate (50 mL) and water (10 mL). were then added. The layers were separated and the organic layer was concentrated under vacuum. The residual oil was chromatographed over silica gel to afford the indole as a white solid.

Examples 10–16

According to the procedure of Example 9 and employing the appropriate 2-trimethylsilyl indole product prepared according to the procedures of Examples 2 through 8, the following 2-unsubstituted indoles are prepared.

| Example | 2-TMS-indole | Indole Product |
|---|---|---|
| 10 | [triazolylmethyl-indole with 3-(2-NMe₂-ethyl), 2-SiMe₃] | [triazolylmethyl-indole with 3-(2-NMe₂-ethyl)] |
| 11 | MeHNO₂S-CH₂-[indole with 3-(2-NMe₂-ethyl), 2-SiMe₃] | MeHNO₂S-CH₂-[indole with 3-(2-NMe₂-ethyl)] |

| Example | 2-TMS-indole | Indole Product |
|---|---|---|
| 12 | | |
| 13 | | |
| 14 | | |
| 15 | | |
| 16 | | | wherein $R^{17}$ is a hydroxy protecting group that is removable under mild acid hydrolysis.

Reference Example A

Preparation of O-t-butyldimethylsilyl-2,2-dimethyl-2-sila-hexan-3-one-6-ol

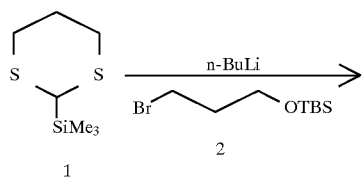

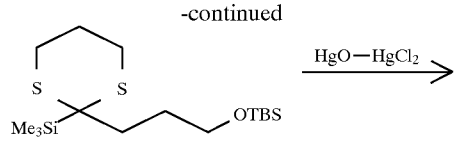

To 5 g (25.98 mmol) of TMS dithiane 1 in 70 mL dry THF at −78° C. was added n-BuLi (1.6M, 16.25 mL, 26 mmol) dropwise. The mixture was warmed to −20° C. and aged at −20° C. for 0.5 h and cooled to −78° C. Bromoether 2 in 5 mL of THF was added dropwise. The mixture was warmed to room temperature and aged for 12 h. It was partitioned between heptane (250 mL) and water (200 mL). The heptane layer was separated and concentrated under vacuum to give the dithiane 3 as a pale yellow oil. A portion of this material was directly used in the next step.

A mixture of dithiane 3 (4.0 g, 11 mmol), mercuric oxide (8.0 g) and mercuric chloride (8.0 g) in acetonitrile-H$_2$O (80:20, 30 mL) and ethyl acetate (10 mL) was aged at room temperature for 0.5 h. The solid was filtered and washed with ethyl acetate (40 mL). The filtrate and wash were combined and concentrated to an oil. This material was chromatographed over silica gel to give the acyl silane 4 as a pale yellow oil.

While the invention has been described and illustrated with reference to certain particular embodiments thereof, those skilled in the art will appreciate that various changes, modifications and substitutions can be made therein without departing from the spirit and scope of the invention. It is intended, therefore, that the invention be defined by the scope of the claims which follow and that such claims be interpreted as broadly as is reasonable.

What is claimed is:

1. A process for preparing a compound of structural formula III:

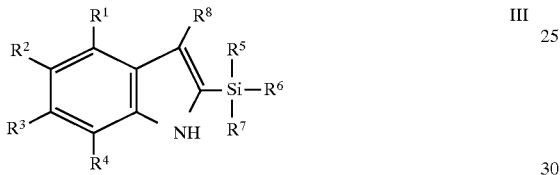

comprising reacting a compound of structural formula I with an acylsilane of structural formula II:

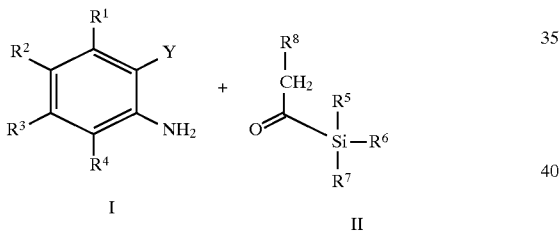

in the presence of a palladium catalyst and a proton acceptor, wherein:

Y is selected from Br, I and triflate, and

R$^1$, R$^2$, R$^3$ and R$^4$ are each independently selected from:
(1) hydrogen;
(2)

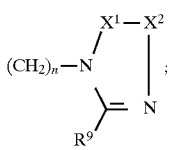

(3) C$_{1-6}$ alkyl;
(4) —(CH$_2$)$_n$—Z
wherein Z represents:
(a) hydrogen,
(b) halogen,
(c) cyano,
(d) nitro,
(e) trifluoromethyl,
(f) —OR$^{10}$,
(g) —OCOR$^{10}$,
(h) —OCONR$^{10}$R$^{11}$,
(i) —OCH$_2$CN,
(j) —OCH$_2$CONR$^{10}$R$^{11}$,
(k) —SR$^{10}$,
(l) —SOR$^{10}$,
(m) —SO$_2$R$^{10}$,
(n) —SO$_2$NR$^{10}$R$^{11}$,
(o) —NR$^{10}$R$^{11}$,
(p) —NR$^{10}$COR$^{11}$,
(q) —NR$^{10}$CO$_2$R$^{11}$,
(r) —NR$^{10}$SO$_2$R$^{11}$,
(s) —COR$^{10}$,
(t) —CO$_2$R$^{10}$,
(u) —CONR$^{10}$R$^{11}$, Or a group of formula (Za), (Zb), (Zc), or (Zd):

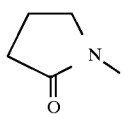

(Za)

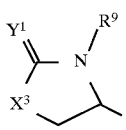

(Zb)

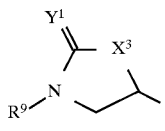

(Zc)

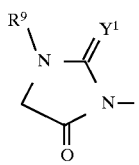

(Zd)

or Z represents an optionally substituted five-membered heteroaromatic ring selected from furan, thiophene, pyrrole, oxazole, thiazole, isoxazole, isothiazole, imidazole, pyrazole, oxadiazole, thiadiazole, triazole and tetrazole;

R$^5$, R$^6$, and R$^7$ are each independently selected from:
(1) C$_{1-6}$ alkyl, and
(2) phenyl;

R$^8$ is selected from:
(1) hydrogen,
(2) —R$^{19}$—OH,
(3) —R$^{19}$—O—R$^{17}$, and
(4) —R$^{19}$NR$^{12}$R$^{13}$, and
(5) —R$^{19}$—Z$^1$
wherein: Z$^1$ is a 3 to 7 membered heterocyclic ring wherein the ring members are selected from 1 to 2 nitrogen atoms and wherein the heterocyclic ring may be subsituted by one or more R$^{14}$;

R$^9$ is selected from:
(1) hydrogen, and
(2) C$_{1-4}$ alkyl;

R$^{10}$ and R$^{11}$ are each independently selected from:
(1) hydrogen,
(2) C$_{1-6}$ alkyl,
(3) trifluoromethyl,
(4) phenyl, optionally substituted with one or more R$^{20}$ substituents
(5) methylphenyl, optionally substituted with one or more R$^{20}$ substituents, and (6) an arylC$_{1-6}$alkyl- or heteroaryl C$_{1-6}$alkyl- group, optionally substituted with one or more R$^{20}$ substituents, or R$^{10}$ and R$^{11}$ when linked through a nitrogen atom, together represent the residue of an optionally substituted azetidine, pyrrolidine, piperidine, morpholine or piperazine ring, optionally substituted with one or more R$^{18}$ substituents;

R$^{12}$ and R$^{13}$ are each independently selected from:
(1) C$_{1-4}$ alkyl,
(2) C$_6$aryl-C$_{1-4}$ alkyl- wherein aryl may be unsubstituted or substituted with one to three substituents selected from methyl, halo, and halomethyl, R$^{14}$ is selected from:
(1) aryl-C$_{1-6}$alkyl-, unsubstituted or substituted with one to three R$^{20}$ substitutents, and
(2) heteroaryl-C$_{1-6}$alkyl-, unsubstituted or substituted with one to three R$^{20}$ substitutents, R$^{15}$ and R$^{16}$ are each independently selected from
(1) hydrogen,
(2) C$_{1-6}$alkyl,
(3) C$_{3-7}$cycloalkyl,
(4) C$_{3-7}$cycloalkylC$_{1-6}$alkyl-,
(5) indanyl,
(6) aryl,
(7) arylC$_{1-6}$alkyl-,
(8) C$_{3-7}$heterocycloalkyl-,
(9) C$_{3-7}$heterocycloalkylC$_{1-6}$alkyl-,
(10) heteroaryl, and
(11) heteroarylC$_{1-6}$alkyl-;

R$^{17}$ is selected from a hydroxy protecting group that is removable under mild acid hydrolysis;

R$^{18}$ is selected from:
(1) C$_{1-6}$alkyl-,
(2) arylC$_{1-6}$alkyl-,
(3) C$_{1-6}$alkoxy-,
(4) C$_{2-6}$alkyoxycarbonyl-, and
(5) C$_{1-6}$alkylaminocarbonyl-;

R$^{19}$ is a straight or branched C$_{1-6}$alkyl chain, optionally substituted with hydroxy or OR$^{17}$;

R$^{20}$ is selected from:
(1) fluoro,
(2) cyano,
(3) trifluoromethyl,
(4) C$_{1-6}$alkyl,
(5) haloC$_{1-6}$alkyl,
(6) aryl,
(7) triazolyl,
(8) tetrazolyl,
(9) tetrazolyl-C$_{1-6}$alkyl-,
(10) hydroxy,
(11) C$_{1-6}$alkoxy-,
(12) C$_{1-6}$alkylthio,
(13) C$_{2-6}$alkoxycarbonyl-,
(14) C$_{2-6}$alkylcarbonyl-,
(15) C$_{1-6}$alkylsulphonyl-,
(16) arylsulfonyl-,
(17) C$_{2-6}$alkylcarbonylamino-,
(18) arylcarbonylamino-,
(19) C$_{2-6}$alkoxycarbonylamino-,
(20) N—C$_{1-6}$alkyl-N—C$_{2-6}$alkoxyamino-,
(21) carbonylamino-,
(22) mono- or diarylaminocarbonylamino-,
(23) pyrrolidinylcarbonylamino-,
(24) piperidinylcarbonylamino-,
(25) aminocarbonyl-,
(26) aminocarbonylamino-,
(27) C$_{1-6}$alkylaminocarbonyl-,
(28) C$_{1-6}$alkylaminocarbonylamino-,
(29) diC$_{1-6}$alkylaminocarbonyl-,
(30) diC$_{1-6}$alkylaminocarbonylamino-,
(31) pyrrolidinylcarbonylamino-,
(32) piperidinylcarbonylamino-,
(33) aminosulfonyl-,
(34) C$_{1-6}$alkylaminosulfonyl-,
(35) C$_{1-6}$alkylsulfonylamino-,
(36) C$_{1-6}$alkylsulfonylaminomethyl-,
(37) arylsulfonylamino-,
(38) diC$_{1-6}$alkylaminosulfonyl-,
(39) aminosulphonylmethyl-,
(40) C$_{1-6}$alkylaminosulfonylmethyl-,
(41) diC$_{1-6}$alkylaminosulfonylmethyl-,
(42) —(CH$_2$)$_m$OR$^{15}$,
(43) —(CH$_2$)$_m$SR$^{15}$,
(44) —(CH$_2$)$_m$SOR$^{15}$,
(45) —(CH$_2$)$_m$SO$_2$R$^{15}$,
(46) —(CH$_2$)$_m$NR$^{15}$R$^{16}$,
(47) =O, and
(48)

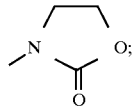

X$^1$ and X$^2$ are each independently selected from ring nitrogen or ring carbon atoms;

X$^3$ is selected from the group consisting of oxygen, sulfur, —NH— or methylene;

Y$^1$ is oxygen or sulfur;

n is an integer independently selected at each occurrence from 0 to 4; and m is an integer selected independently each occurrence from 0 to 4.

2. The process according to claim 1 wherein R$^1$, R$^3$, and R$^4$ are each hydrogen.

3. The process according to claim 1 wherein the palladium catalyst is selected from: a palladium alkanoate, a palladium acetonate, a palladium halide, a palladium halide complex, a palladium-benzylidine acetone complex and a triarylphosphine palladium complex.

4. The process according to claim 3 wherein the palladium catalyst is selected from: Pd(II) acetate, Pd(II) acetylacetonate, Pd(O)bis-dibenzylidene acetone ("dba"), Pd(II) bromide, Pd(II) chloride, Pd(II) iodide, Pd(II) sulfate, Pd(II)trifluoroacetate, Pd(II) Cl$_2$(CH$_3$CN)$_2$, Pd$_2$ (dba)$_3$, and Pd(II)Cl$_2$(PhCN)$_2$.

5. The process according to claim 4 wherein the palladium catalyst is Pd(II) acetate.

6. The process according to claim 1 wherein the proton acceptor does not interact with the palladium catalyst to inhibit its catalytic activity.

7. The process according to claim 6 wherein the proton acceptor is selected from:
(a) an alkylamine,
(b) an aromatic amine,
(c) a heterocyclic amine, and
(d) a phosphate.

8. The process according to claim 7 wherein the proton acceptor is an alkylamine.

9. The process according to claim 8 wherein the alkylamine is selected from:

(a) 1,4-diazobicyclo[2.2.2]octane,
(b) quinuclidine,
(c) t-butylamine,
(d) 2,2,6,6-tetramethylpiperidine, and
(e) di-t-butylamine.

10. The process according to claim 9 wherein the alkylamine is 1,4-diazobicyclo[2.2.2]octane.

11. The process according to claim 1 wherein the reaction is carried out in a dry organic solvent inert for the starting materials.

12. The process according to claim 11 wherein the solvent is selected from:
(a) DMSO,
(b) DMF,
(c) DMAC, and
(d) NMP.

13. The process according to claim 12 wherein the solvent is DMF.

14. The process according to claim 11 wherein the reaction is carried out at a temperature of 90° C. to 120° C.

15. The process according to claim 1 additionally comprising the step of deprotecting the compound of structural formula (III) to obtain the compound of structural formula (IV):

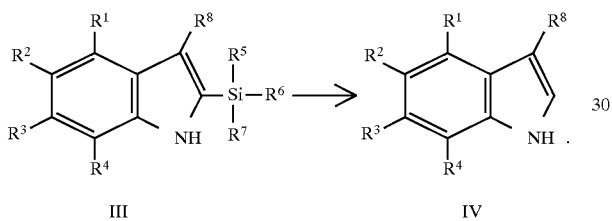

16. The process according to claim 15 wherein the deprotection is a Lewis-acid catalyzed deprotection.

17. The process according to claim 15 wherein:
$R^1$, $R^2$, $R^3$ and $R^4$ are each independently selected from:
(1) hydrogen;
(2)

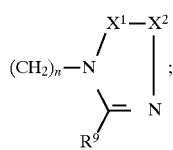

(3) $C_{1-6}$ alkyl;
(4) —$(CH_2)_n$—Z
wherein Z represents:
(a) hydrogen,
(b) halogen,
(c) cyano,
(d) nitro,
(e) trifluoromethyl,
(f) $OR^{10}$,
(g) $OCOR^{10}$,
(h) $OCONR^{10}R^{11}$,
(i) $OCH_2CN$,
(j) $OCH_2CONR^{10}R^{11}$,
(k) $SR^{10}$, provided that $R^{10}$ is not hydrogen,
(l) $SOR^{10}$,
(m) $SO_2R^{10}$,
(n) $SO_2NR^{10}R^{11}$,
(o) $NR^{10}R^{11}$,
(p) $NR^{10}COR^{11}$,
(q) $NR^{10}CO_2R^{11}$,
(r) $NR^{10}SO_2R^{11}$,
(s) $COR^{10}$,
(t) $CO_2R^{10}$,
(u) $CONR^{10}R^{11}$,
or Z is a group of formula (Za), (Zb), (Zc), or (Zd):

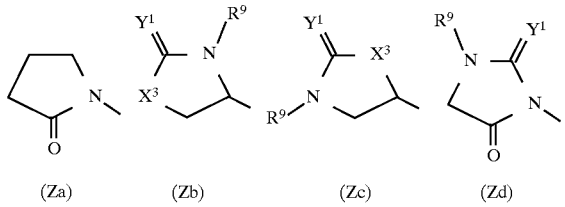

(Za)    (Zb)    (Zc)    (Zd)

or Z represents an optionally substituted five-membered heteroaromatic ring selected from furan, thiophene, pyrrole, oxazole, thiazole, isoxazole, isothiazole, imidazole, pyrazole, oxadiazole, thiadiazole, triazole and tetrazole;

$R^5$, $R^6$, and $R^7$ are each independently selected from:
(1) $C_{1-6}$ alkyl,
(2) —O—$C_{1-6}$ alkyl, and
(2) phenyl;

$R^8$ is selected from:
(1) hydrogen,
(2) —$R^{19}$—OH,
(3) —$R^{19}$—O—$R^{17}$, and
(4) —$R^{19}NR^{12}R^{13}$, and
(5) —$R^{19}$—$Z^1$
wherein: $Z^1$ is a 3 to 7 membered heterocyclic ring wherein the ring members are selected from 1 to 2 nitrogen atoms and wherein the heterocyclic ring may be subsituted by one or more $R^{14}$;

$R^9$ is selected from:
(1) hydrogen, and
(2) $C_{1-4}$ alkyl;

$R^{10}$ and $R^{11}$ are each independently selected from:
(1) hydrogen,
(2) $C_{1-6}$ alkyl,
(3) trifluoromethyl,
(4) phenyl, optionally substituted with one or more $R^{20}$ substituents
(5) methylphenyl, optionally substituted with one or more $R^{20}$ substituents, and
(6) an aryl$C_{1-6}$alkyl or heteroaryl $C_{1-6}$alkyl group, optionally substituted with one or more $R^{20}$ substituents, or $R^{10}$ and $R^{11}$ when linked through a nitrogen atom, together represent the residue of an optionally substituted azetidine, pyrrolidine, piperidine, morpholine or piperazine ring, optionally substituted with one or more $R^{18}$ substituents;

$R^{12}$ and $R^{13}$ are each independently selected from:
(1) $C_{1-4}$ alkyl,
(2) $C_{1-4}$ alkyl-$C_6$aryl wherein aryl may be unsubstituted or substituted with one to three substituents selected from methyl, halo, and halomethyl, $R^{14}$ is selected from:
(1) aryl-$C_{1-6}$alkyl, unsubstituted or substituted with one to three $R^{20}$ substitutents, and
(2) heteroaryl-$C_{1-6}$alkyl, unsubstituted or substituted with one to three $R^{20}$ substitutents, $R^{15}$ and $R^{16}$ are each independently selected from (1) hydrogen,
(2) $C_{1-6}$alkyl,
(3) $C_{3-7}$cycloalkyl,
(4) $C_{3-7}$cycloalkyl$C_{1-6}$alkyl,
(5) indanyl,
(6) aryl,
(7) aryl$C_{1-6}$alkyl,
(8) $C_{3-7}$heterocycloalkyl,
(9) $C_{3-7}$heterocycloalkyl$C_{1-6}$alkyl,
(10) heteroaryl, and
(11) heteroaryl$C_{1-6}$alkyl;

$R^{17}$ is selected from a hydroxy protecting group that is removable under mild acid hydrolysis;

$R^{18}$ is selected from:
(1) $C_{1-6}$alkyl,
(2) aryl$C_{1-6}$alkyl,
(3) $C_{1-6}$alkoxy,
(4) $C_{2-6}$alkyoxycarbonyl, and
(5) $C_{1-6}$alkylaminocarbonyl;

$R^{19}$ is a straight or branched $C_{1-6}$alkyl chain;

$R^{20}$ is selected from:
(1) fluoro,
(2) cyano,
(3) trifluoromethyl,
(4) $C_{1-6}$alkyl,
(5) halo$C_{1-6}$alkyl,
(6) aryl,
(7) triazolyl,
(8) tetrazolyl,
(9) $C_{1-6}$alkyl-tetrazolyl,
(10) hydroxy,
(11) $C_{1-6}$alkoxy,
(12) $C_{1-6}$alkylthio,
(13) $C_{2-6}$alkoxycarbonyl,
(14) $C_{2-6}$alkylcarbonyl,
(15) $C_{1-6}$alkylsulphonyl,
(16) arylsulfonyl,
(17) $C_{2-6}$alkylcarbonylamino,
(18) arylcarbonylamino,
(19) $C_{2-6}$alkoxycarbonylamino,
(20) N—$C_{1-6}$alkyl-N—$C_{2-6}$alkoxyamino,
(21) carbonylamino,
(22) mono- or diarylaminocarbonylamino,
(23) pyrrolidinylcarbonylamino,
(24) piperidinylcarbonylamino,
(25) aminocarbonyl,
(26) aminocarbonylamino,
(27) $C_{1-6}$alkylaminocarbonyl,
(28) $C_{1-6}$alkylaminocarbonylamino,
(29) di$C_{1-6}$alkylaminocarbonyl,
(30) di$C_{1-6}$alkylaminocarbonylamino,
(31) pyrrolidinylcarbonylamino,
(32) piperidinylcarbonylamino,
(33) aminosulfonyl,
(34) $C_{1-6}$alkylaminosulfonyl,
(35) $C_{1-6}$alkylsulfonylamino,
(36) $C_{1-6}$alkylsulfonylaminomethyl,
(37) arylsulfonylamino,
(38) di$C_{1-6}$alkylaminosulfonyl,
(39) aminosulphonylmethyl,
(40) $C_{1-6}$alkylaminosulfonylmethyl, and
(41) di$C_{1-6}$alkylaminosulfonylmethyl,
(42) $(CH_2)_mOR^{15}$,
(43) $(CH_2)_mSR^{15}$, provided that $R^{15}$ is not hydrogen,
(44) $(CH_2)_mSOR^{15}$,
(45) $(CH_2)_mSO_2R^{15}$,
(46) $(CH_2)_mNR^{15}R^{16}$,
(47) =O, and
(48)

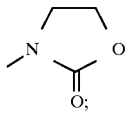

$X^1$ and $X^2$ are each independently selected from ring nitrogen or ring carbon atoms;

$X^3$ is selected from the group consisting of oxygen, sulfur, —NH— or methylene;

$Y^1$ is oxygen or sulfur;

n is an integer independently selected at each occurrence from 0 and 1; and m is an integer selected independently at each occurrence from 0 to 4.

18. The process according to claim 17 wherein $R^1$, $R^3$, and $R^4$ are each hydrogen.

19. The process according to claim 18 wherein the compound according to structural formula IV is selected from:

(1) 1-benzyl-4-[3-(5-(1,2,4-triazol-4-yl)-1H-indol-3-yl)propyl]piperazin-2-one;
(2) 1-(2-phenylethyl)-4-[3-(5-(1,2,4-triazol-4-yl)-1H-indol-3-yl)propyl]piperazin-2-one;
(3) 1-[2-(3-fluorophenyl)ethyl]-4-[3-(5-(1,2,4-triazol-4-yl)-1H-indol-3-yl)propyl]piperazin-2-one;
(4) (3S)-3-(N-benzyl)aminomethyl-1-[2-(5-(N-methyl)-aminosulphonylmethyl)-1H-indol-3-yl)ethyl]pyrrolidine;
(5) (3S)-3-(N-benzyl)aminomethyl-1-[2-(5-(aminosulphonyl-methyl)-1H-indol-3-yl)ethyl]pyrrolidine;
(6) (3S)-3-(N-benzyl)aminomethyl-(S)-1-[2-(5-(2-oxo-1,3-oxazolidin-4-ylmethyl)-1H-indol-3-yl)ethyl]pyrrolidine;
(7) (3S)-3-[N-(R)-α-(hydroxymethyl)benzyl]aminomethyl-(S)-1-[2-(5-(2-oxo-1,3-oxazolidin-4-ylmethyl)-1H-indol-3-yl)ethyl]pyrrolidine;
(8) (3S)-3-[N-(S)-α-methylbenzyl]aminomethyl-(S)-1-[2-(5-(2-oxo-1,3-oxazolidin-4-ylmethyl)-1H-indol-3-yl)ethyl]pyrrolidine;
(9) 4-[N-(R)-(α-(hydroxymethyl)benzyl]amino-(S)-1-[3-(5-(2-oxo-1,3-oxazolidin-4-ylmethyl)-1H-indol-3-yl)propyl]piperidine;
(10) (3S)-3-(N-benzyl-N-methyl)aminomethyl-(S)-1-[2-(5-(3-methyl-2-oxo-1,3-oxazolidin-4-ylmethyl)-1H-indol-3-yl)ethyl]pyrrolidine;
(11) (3R)-3-[N-(S)-α-methylbenzyl-N-methyl]aminomethyl-(S)-1-[2-(5-(2-oxo-1,3-oxazolidin-4-ylmethyl)-1H-indol-3-yl)ethyl]pyrrolidine;
(12) (3R)-3-[N-(S)-(α-methylbenzyl-N-methyl]aminomethyl-(S)-1-[2-(5-(3-methyl-2-oxo-1,3-oxazolidin-4-ylmethyl)-1H-indol-3-yl)ethyl]pyrrolidine;
(13) (3S)-3-[N-(4-fluorobenzyl)-N-methyl]aminomethyl-(S)-1-[2-(5-(3-methyl-2-oxo-1,3-oxazolidin-4-ylmethyl)-1H-indol-3-yl)ethyl]pyrrolidine;
(14) 4-benzyl 12-{2-fluoromethyl-3-(5-(1,2,4-triazol-4-yl)-1H-indol-3-yl)propyl]piperazine;
(15) 4-[2-(3-fluorophenyl)ethyl]-1-[2-fluoro-3-(5-(1,2,4-triazol-4-yl)-1H-indol-3-yl)propyl]piperazine;
(16) 4-benzyl-1-[2-fluoro-3-(5-(1,2,4-triazol-4-yl)-1H-indol-3-yl)propyl]piperidine;

(17) 4-(N-benzyl-N-methylamino)-1-[2-fluoro-3-(5-(1,2,4-triazol-4-yl)-1H-indol-3-yl)propyl]piperidine;

(18) 4-[(R)-2-hydroxy-1-(4-fluorophenyl)ethylamino]-1-[2-fluoro-3-(5-(1,2,4-triazol-4-yl)-1H-indol-3-yl)propyl]piperidine;

(19) 7-benzyl-2-[2-(5-(1,2,4-triazol-4-yl)-1H-indol-3-yl)ethyl]-cis-2,7-diazabicyclo[3.3.0]octane;

(20) 7-(3-furylmethyl-2-[2-(5-(1,2,4-triazol-4-yl)-1H-indol-3-yl)ethyl]-cis-2,7-diazabicyclo[3.3.0]octane;

(21) 7-(2-phenylethyl)-2-[2-(5-(1,2,4-triazol-4-yl)-1H-indol-3-yl)ethyl]-cis-2,7-diazabicyclo[3.3.0]octane;

(22) 7-(4-fluorobenzyl-2-[2-(5-(1,2,4-triazol-4-yl)-1H-indol-3-yl)ethyl]-cis-2,7-diazabicyclo[3.3.0]octane;

(23) 7-(2,4-difluorobenzyl-2-[2-(5-(1,2,4-triazol-4-yl)-1H-indol-3-yl)ethyl]-cis-2,7-diazabicyclo[3.3.0]octane;

(24) 4-(2,2-difluoro-1-oxo-2-phenylethyl)-1-[3-(5-(1,2,4-triazol-4-yl)-1H-indol-3-yl)propyl]piperazine;

(25) 4-benzyl-3-methyl-1-[3-(5-(1,2,4-triazol-4-yl)-1H-indol-3-yl)propyl]-1,2,5,6-tetrahydropyridine;

(26) 4-benzyl-3-methoxymethyl-1-[3-(5-(1,2,4-triazol-4-yl)-1H-indol-3-yl)propyl]-1,2,5,6-tetrahydropyridine;

(27) 1-(2-hydroxy-1-phenylethyl)-4-[3-(5-(1,2,4-triazol-4-yl)-1H-indol-3-yl)propyl]piperidine;

(28) 1-[2-(2-fluorophenyl)ethyl]-4-[3-(5-(1,2,4-triazol-4-yl)-1H-indol-3-yl)propyl]piperidine;

(29) 1-benzyl-4-[3-(5-(1,2,4-triazol-4-yl)-1H-indol-3-yl)propyl]piperidine;

(30) 1-(3,3-dimethylbutyl)-4-[3-(5-(1,2,4-triazol-4-yl)-1H-indol-3-yl)propyl]piperidine;

(31) 1-(2-phenylethyl)-4-[3-(5-(1,2,4-triazol-4-yl)-1H-indol-3-yl)propyl]piperidine;

(32) 1-cyclohexylmethyl-4-[3-(5-(1,2,4-triazol-4-yl)-1H-indol-3-yl)propyl]piperidine;

(33) 1-(3-phenylpropyl)-4-[3-(5-(1,2,4-triazol-4-yl)-1H-indol-3-yl)propyl]piperidine;

(34) 1-[2-(3-fluorophenyl)ethyl]-4-[3-(5-(1,2,4-triazol-4-yl)-1H-indol-3-yl)propyl]piperidine;

(35) 1-[2-(4-trifluoromethylphenyl)ethyl]-4-[3-(5-(1,2,4-triazol-4-yl)-1H-indol-3-yl)propyl]piperidine;

(36) 1-[2-(3,4-difluorophenyl)ethyl]-4-[3-(5-(1,2,4-triazol-4-yl)-1H-indol-3-yl)propyl]piperidine;

(37) N-methyl-2-phenyl-2-[4-(3-(5-(1,2,4-triazol-4-yl)-1H-indol-3-yl)propyl)piperidin-1-yl]acetamide;

(38) 1-(2-oxo-2-phenylethyl)-4-[3-(5-(1,2,4-triazol-4-yl)-1H-indol-3-yl)propyl]piperidine;

(39) 1-(2-phenylpropyl)-4-[3-(5-(1,2,4-triazol-4-yl)-1H-indol-3-yl)propyl]piperidine;

(40) 4-benzyl-4-fluoro-1-[3-(5-(1,2,4-triazol-4-yl)-1H-indol-3-yl)propyl]piperidine;

(41) 4-fluoro-4-[2-(3-fluorophenyl)ethyl]-1-[3-(5-(1,2,4-triazol-4-yl)-1H-indol-3-yl)propyl]piperidine;

(42) 4-fluoro-4-(3-fluorobenzyl)-1-[3-(5-(1,2,4-triazol-4-yl)-1H-indol-3-yl)propyl]piperidine;

(43) 4-fluoro-4-(2-fluorobenzyl)-1-[3-(5-(1,2,4-triazol-4-yl)-1H-indol-3-yl)propyl]piperidine;

(44) 4-benzyl-4-methoxy-1-[3-(5-(1,2,4-triazol-4-yl)-1H-indol-3-yl)propyl]piperidine;

(45) 4-benzyl-4-methoxy-1-[3-(5-(1,2,4-triazol-1-ylmethyl)-1H-indol-3-yl)propyl]piperidine;

(46) 4-(2-fluorobenzyl)-4-methoxy-1-[3-(5-(1,2,4-triazol-4-yl)-1H-indol-3-yl)propyl]piperidine;

(47) 4-(3-fluorobenzyl)-4-methoxy-1-[3-(5-(1,2,4-triazol-4-yl)-1H-indol-3-yl)propyl]piperidine;

(48) 4-(4-fluorobenzyl)-4-methoxy-1-[3-(5-(1,2,4-triazol-4-yl)-1H-indol-3-yl)propyl]piperidine;

(49) 1-[3-(5-(1,2,4-triazol-4-yl)-1H-indol-3-yl)propyl]-4-[2-(oxazol-2-on-3-yl)-1-phenylethyl]piperazine;

(50) 1-[3-(5-(1,2,4-triazol-4-yl)-1H-indol-3-yl)propyl]-4-[2-(oxazolidin-2-on-3-yl)-1-phenylethyl]piperazine;

(51) 1-[3-(5-(1,2,4-triazol-4-yl)-1H-indol-3-yl)propyl]-4-[1-(4-fluorophenyl)-2-(oxazolidin-2-on-3-yl)ethyl]piperazine;

(52) 1-[3-(5-(1,2,4-triazol-4-yl)-1H-indol-3-yl)propyl]-4-(3-hydroxy-1-phenylpropyl)piperazine;

(53) 1-[3-(5-(1,2,4-triazol-4-yl)-1H-indol-3-yl)propyl]-4-[2-(imidazol-1-yl)-1-phenylethyl]piperazine;

(54) 1-[3-(5-(1,2,4-triazol-4-yl)-1H-indol-3-yl)propyl]-4-[1-(4-fluorophenyl)-2-hydroxyethyl]piperazine;

(55) 1-[3-(5-(1,2,4-triazol4-yl)-1H-indol-3-yl)propyl]-4-[1-(4-fluorophenyl)-2-methoxyethyl]piperazine;

(56) 1-[3-(5-(1,2,4-triazol-4-yl)-1H-indol-3-yl)propyl]-4-[3-(5-methyl-1,2,4-oxadiazol-3-yl)-1-phenylpropyl]piperazine;

(57) 1-[3-(5-(1,2,4-triazol-4-yl)-1H-indol-3-yl)propyl]-4-[2-benzyloxy-1-(4-fluorophenyl)ethyl]piperazine;

(58) 1-[3-(5-(1,2,4-triazol-4-yl)-1H-indol-3-yl)propyl]-4-[1-(4fluorophenyl)-3-methoxypropyl]piperazine;

(59) 1-[3-(5-(1,2,4-triazol-4-yl)-1H-indol-3-yl)propyl]-4-[1-(4-fluorophenyl)-2-(imidazol-1-yl)ethyl]piperazine;

(60) 1-[3-(5-(1,2,4-triazol-4-yl)-1H-indol-3-yl)propyl]-4-[1-phenyl-2-(pyrrolidin-1-yl)ethyl]piperazine;

(61) 1-[3-(5-(1,2,4-triazol-4-yl)-1H-indol-3-yl)propyl]-4-[1-(4-fluorophenyl)-3-hydroxypropyl]piperazine;

(62) 1-[3-(5-(1,2,4-triazol-4-yl)-1H-indol-3-yl)propyl]-4-[3-(imidazol-1-yl)-1-phenylpropyl]piperazine;

(63) 1-[3-(5-(1,2,4-triazol-4-yl)-1H-indol-3-yl)propyl]-4-(3-hydroxy-2-phenylpropyl)piperazine;

(64) 1-[3-(5-(1,2,4-triazol-4-yl)-1H-indol-3-yl)propyl]-4-(3-methoxy-2-phenylpropyl)piperazine;

(65) 1-[3-(5-(1,2,4-triazol-4-yl)-1H-indol-3-yl)propyl]-4-[2-(4-fluorophenyl)-3-hydroxypropyl]piperazine;

(66) 1-[3-(5-(1,2,4-triazol-4-yl)-1H-indol-3-yl)propyl]-4-[1-(4-fluorophenyl)prop-2-yl]piperazine;

(67) 1-[3-(5-(1,2,4-triazol-4-yl)-1H-indol-3-yl)propyl]-4-[2-(4-fluorophenyl)propyl]piperazine;

(68) 1-[3-(5-(1,2,4-triazol-4-yl)-1H-indol-3-yl)propyl]-4-[1-(4-fluorophenyl)-3-hydroxyprop-2-yl]piperazine;

(69) 1-[3-(5-(1,2,4-triazol-4-yl)-1H-indol-3-yl)propyl]-4-[1-(4-fluorophenyl)-3-methoxyprop-2-yl]piperazine;

(70) 1-[3-(5-(1,2,4-triazol-4-yl)-1H-indol-3-yl)propyl]-4-[2-(3-fluorophenyl)-ethyl]piperazine;

(71) 1-[3-(5-(1,2,4-triazol-4-yl)-1H-indol-3-yl)propyl]-4-[2-(2-fluorophenyl)-ethyl]piperazine;

(72) 1-[3-(5-(1,2,4-triazol-4-yl)-1H-indol-3-yl)propyl]-4-[2-(4-fluorophenyl)-ethyl]piperazine;

(73) 1-[3-(5-(1,2,4-triazol-4-yl)-1H-indol-3-yl)propyl]-4-[2-(3-methoxyphenyl)-ethyl]piperazine;

(74) 1-[3-(5-(1,2,4-triazol-4-yl)-1H-indol-3-yl)propyl]-4-[2-(3-trifluoromethyl-phenyl)ethyl]piperazine;

(75) 1-[3-(5-(1,2,4-triazol-4-yl)-1H-indol-3-yl)propyl]-4-[2-(3,4-difluorophenyl)-ethyl]piperazine;

(76) 1-[3-(5-(1,2,4-triazol-4-yl)-1H-indol-3-yl)propyl]-4-[2-(2,4-difluorophenyl)-ethyl]piperazine;

(77) 1-[3-(5-(1,2,4-triazol-4-yl)-1H-indol-3-yl)propyl]-4-[2-(3,5-difluorophenyl)-ethyl]piperazine;

(78) 1-[3-(5-(1,2,4-triazol-4-yl)-1H-indol-3-yl)propyl]-4-[2-(3-(oxazolidin-2-on-3-yl)phenyl)ethyl]piperazine;

(79) N-methyl-3-[5-(1,2,4-triazol-4-yl)-1H-indol-3-yl]pyrrolidine;

(80) N-methyl-4-[5-(1,2,4-triazol-4-yl)-1H-indol-3-yl]piperidine;

(81) N,N-dimethyl-2-[5-(1,2,4-triazol-4-yl)-1H-indol-3-yl]ethylamine;

(82) 4-(1-phenylethyl)-1-[3-(5-(1,2,4-triazol-4-yl)-1H-indol-3-yl)propyl]-1,2,5,6-tetrahydropyridine;

(83) 4-(α-isopropyloxy)phenylmethyl-1-[3-(5-(1,2,4-triazol-4-yl)-1H-indol-3-yl)propyl]-1,2,5,6-tetrahydropyridine;

(84) 4-(α-methoxy)phenylmethyl-1-[3-(5-(1,2,4-triazol-4-yl)-1H-indol-3-yl)propyl]-1,2,5,6-tetrahydropyridine;

(85) 4-[α-(2-methoxyethyl)oxy]phenylmethyl-1-[3-(5-(1,2,4-triazol-4-yl)-1H-indol-3-yl)propyl]-1,2,5,6-tetrahydropyridine;

(86) 4-benzyl-1-[3-(2,3-dihydro-5-(1,2,4-triazol-4-yl)-1H-indol-3-yl)propyl]piperazine;

(87) 1-[3-(2,3-dihydro-5-(1,2,4-triazol-4-yl)-1H-indol-3-yl)propyl]-4-(pyridin-3-ylmethyl)piperazine;

(88) 1-[2-(5-(I,1,2,4-triazol-4-yl)-1H-indol-3-yl)propyl]-4-[2-(4-fluorophenyl)-4-methylpiperazin-1-yl]piperidine;

(89) 1-[2-(5-(1,2,4-triazol-1-ylmethyl)-1H-indol-3-yl)ethyl]-3(R)-(3(R)-phenylmorpholin-4-ylmethyl)pyrrolidine;

(90) 1-[3-(5-(1,2,4-triazol-4-yl)-1H-indol-3-yl)propyl]-4-(3-oxo-2-phenylpiperazin-1-yl)methylpiperidine;

(91) 1-[3-(5-(1,2,4-triazol-4-yl)-1H-indol-3-yl)propyl]-4-(4-methyl-2-phenylpiperazin-1-yl)piperidine;

(92) 1-[3-(5-(1,2,4-triazol-4-yl)-1H-indol-3-yl)propyl]-4-(benzimidazol-2-on-1-yl)piperidine;

(93) 1-[3-(5-(1,2,4-triazol-4-yl)-1H-indol-3-yl)propyl]-4-[6-(4-fluorophenyl)-4-methyl-3-oxopiperazin-1-yl]piperidine;

(94) [3-(3-(4-(2-(3,4-difluorophenyl)ethyl)piperazin-1-yl)propyl)-1H-indol-5-ylmethyl]oxazolidin-2-one;

(95) (S)-4-[3-(3-(4-(2-(3,4-difluorophenyl)ethyl)piperazin-1-yl)propyl)-1H-indol-5-ylmethyl]-3-methyloxazolidin-2-one;

(96) 1-[3-(5-(N-methylaminosulphonylmethyl)-1H-indol-3-yl)propyl]-4-[2-(4-(acetylamino)phenyl)ethyl]piperazine;

(97) 3-benzyl-7-[3-(5-(1,2,4-triazol-4-yl)-1H-indol-3-yl)propyl]-cis-3,7-diazabicyclo[3.3.0]octane;

(98) 3-(pyridin-3-yl)methyl-7-[3-(5-(1,2,4-triazol-4-yl)-1H-indol-3-yl)propyl]-cis-3,7-diazabicyclo[3.3.0]octane;

(99) 3-[2-(4-(acetylamino)phenyl)ethyl]-7-[3-(5-(1,2,4-triazol-4-yl)-1H-indol-3-yl)propyl]-cis-3,7-diazabicyclo[3.3.0]octane;

(100) 3-benzoyl-7-[3-(5-(1,2,4-triazol-4-yl)-1H-indol-3-yl)propyl]-cis-3,7-diazabicyclo[3.3.0]octane;

(101) (1RS,3RS,5RS)-7-benzyl-3-[5-(imidazol-1-yl)-1H-indol-3-ylmethyl]-2-methyl-2,7-diazabicyclo[3.3.0]octane;

(102) (1RS,3RS,5RS)-7-[2-(3-fluorophenyl)ethyl]-2-methyl-3-[5-(1,2,4-triazol-4-yl)-1H-indol-3-ylmethyl]-2,7-diazabicyclo[3.3.0]octane;

(103) (1RS,3RS,5RS)-7-(4-fluorobenzyl)-2-methyl-3-[5-(1,2,4-triazol-4-yl)-1H-indol-3-ylmethyl]-2,7-diazabicyclo[3.3.0]octane;

(104) 4-[1-(phenyl)-N,N-dimethylcarboxamidomethyl]-1-[3-(5-(1,2,4-triazol-4-yl)-1H-indol-3-yl)propyl]piperazine;

(105) 4-(2-methoxycarbonylamino-1-phenylethyl)-1-[3-(5-(1,2,4-triazol-4-yl)-1H-indol-3-yl)propyl]piperazine;

(106) 4-(2-dimethylamino-1-phenylethyl)-1-[3-(5-(1,2,4-triazol-4-yl)-1H-indol-3-yl)propyl]piperazine;

(107) 1-[3-(5-(1,2,4-triazol-4-yl)-1H-indol-3-yl)propyl]-4-(4-fluorophenyl)methylpiperazine;

(108) 4-[2-(N-methyl-N-methoxycarbonyl)amino-1-phenylethyl]-1-[3-(5-(1,2,4-triazol-4-yl)-1H-indol-3-yl)propyl]-piperazine;

(109) 1-benzyl-4-[(R,S)-2-hydroxymethyl-3-(5-(1,2,4-triazol-4-yl)-1H-indol-3-yl)propyl]piperazine;

(110) 1-[3-(5-(1,2,4-triazol-4-yl)-1H-indol-3-yl)propyl]-4-[2-(1H-tetrazol-5-yl)phenyl]methylpiperazine;

(111) 1-[3-(5-(1,2,4-triazol-4-yl)-1H-indol-3-yl)propyl]-4-(2-phenylethyl)piperazine;

(112) 4-benzyl-1-[3-(5-(1,2,4-triazol-4-yl)-1H-indol-3-yl)propyl]piperazine;

(113) 4-[2-(2-methyltetrazol-5-yl)phenyl]methyl-1-[3-(5-(1,2,4-triazol-4-yl)-1H-indol-3-yl)propyl]piperazine;

(114) 4-[2-(1-methyltetrazol-5-yl)phenyl]methyl-1-[3-(5-(1,2,4-triazol-4-yl)-1H-indol-3-yl)propyl]piperazine;

(115) 4-[2-(N-methylcarboxamido)phenyl]methyl-1-[3-(5-(1,2,4-triazol-4-yl)-1H-indol-3-yl)propyl]piperazine;

(116) 4-[2-(N,N-dimethylaminomethyl)phenyl]methyl-1-[3-(5-(1,2,4-triazol-4-yl)-1H-indol-3-yl)propyl]piperazine;

(117) 4-(but-3-enyl)-1-[3-(5-(1,2,4-triazol-4-yl)-1H-indol-3-yl)propyl]piperazine;

(118) 4-(3-methylbut-2-enyl)-1-[3-(5-(1,2,4-triazol-4-yl)-1H-indol-3-yl)propyl]piperazine;

(119) 4-(prop-2-enyl)-1-[3-(5-(1,2,4-triazol-4-yl)-1H-indol-3-yl)propyl]piperazine;

(120) 4-(prop-2-ynyl)-1-[3-(5-(1,2,4-triazol-4-yl)-1H-indol-3-yl)propyl]piperazine;

(121) 4-[(R,S)-1-(phenyl)carboxamidomethyl]-1-[3-(5-(1,2,4-triazol-4-yl)-1H-indol-3-yl)propyl]piperazine;

(122) 4-[1-(phenyl)-N-methylcarboxamidomethyl]-1-[3-(5-(1,2,4-triazol-4-yl)-1H-indol-3-yl)propyl]piperazine;

(123) 1-[3-(5-(1,2,4-triazol-1-ylmethyl)-1H-indol-3-yl)propyl]-4-[2-(4-(acetylamino)phenyl)ethyl]piperazine;

(124) 1-[3-(5-(1,2,4-triazol-4-yl)-1H-indol-3-yl)propyl]-4-[2-(3-(acetylamino)phenyl)ethyl]piperazine;

(125) 1-[3-(5-(1,2,4-triazol-4-yl)-1H-indol-3-yl)propyl]-4-[4-(aminosulphonyl)phenyl]methylpiperazine;

(126) 1-[3-(5-(1,2,4-triazol-4-yl)-1H-indol-3-yl)propyl]-4-(furan-3-yl)methylpiperazine;

(127) 1-[3-(5-(1,2,4-triazol-4-yl)-1H-indol-3-yl)propyl]-4-(furan-2-yl)methylpiperazine;

(128) 1-[3-(5-(1,2,4-triazol-4-yl)-1H-indol-3-yl)propyl]-4-(thien-2-yl)methylpiperazine;

(129) 1-benzyl-4-[(R,S)-2-hydroxy-3-(5-(1,2,4-triazol-4-yl)-1H-indol-3-yl)propyl]piperazine;

(130) 1-[2-(4-(acetylamino)phenyl)ethyl]-4-[(R,S)-2-hydroxy-3-(5-(1,2,4-triazol-4-yl)-1H-indol-3-yl)propyl]piperazine;

(131) 1-[3-(5-(1,2,4-triazol-4-yl)-1H-indol-3-yl)propyl]-4-[2-(4-(aminocarbonylamino)phenyl)ethyl]piperazine;

(132) 1-[3-(5-(1,2,4-triazol-4-yl)-1H-indol-3-yl)propyl]-4-(4-cyanophenyl)methylpiperazine;

(133) 1-[3-(5-(1,2,4-triazol-4-yl)-1H-indol-3-yl)propyl]-4-[2-(4-cyanophenyl)ethyl]piperazine;

(134) 1-[3-(5-(1,2,4-triazol-4-yl)-1H-indol-3-yl)propyl]-4-[2-(4-(1,2,4-triazol-4-yl)phenyl)ethyl]piperazine;

(135) 1-[3-(5-(1,2,4-triazol-1-yl)-1H-indol-3-yl)propyl]-4-[2-(4-(acetylamino)phenyl)ethyl]piperazine;

(136) 1-[3-(5-(1,2,4-triazol-1-yl)-1H-indol-3-yl)propyl]-4-benzylpiperazine;

(137) 1-[3-(5-(1,2,4-triazol-1-ylmethyl)-1H-indol-3-yl)propyl]-4-benzylpiperazine;

(138) 4-(4-acetylaminophenyl)methyl-1-[3-(5-(1,2,4-triazol-4-yl)-1H-indol-3-yl)propyl]piperidine;

(139) 4-benzyl-1-[3-(5-(1,2,4-triazol-4-yl)-1H-indol-3-yl)propyl]-1,2,5,6-tetrahydropyridine;

(140) 1-[3-(5-(1,2,4-triazol-4-yl)-1H-indol-3-yl)propyl]-4-(2-aminopyridine-5-yl)methylpiperazine;

(141) 1-[3-(5-(1,2,4-triazol-4-yl)-1H-indol-3-yl)propyl]-4-(4-aminophenyl)methylpiperazine;

(142) 1-[4-(5-(1,2,4-triazol-4-yl)-1H-indol-3-yl)butyl]-4-benzylpiperazine;

(143) 1-[4-(5-(1,2,4-triazol-4-yl)-1H-indol-3-yl)butyl]-4-(pyridin-2-yl)methylpiperazine;

(144) 1-[4-(5-(1,2,4-triazol-4-yl)-1H-indol-3-yl)butyl]-4-(pyridin-3-yl)methylpiperazine;

(145) 1-[3-(5-(1,2,4-triazol-4-yl)-1H-indol-3-yl)propyl]-4-[2-4-aminophenyl)ethyl]piperazine;

(146) 1-[3-(5-(1,2,4-triazol-4-yl)-1H-indol-3-yl)propyl]-4-[2-(4-(acetylamino)phenyl)ethyl]piperazine;

(147) 1-[3-(5-(1,2,4-triazol-4-yl)-1H-indol-3-yl)propyl]-4-(imidazol-2-yl)methylpiperazine;

(148) 1-[3-(5-(1,2,4-triazol-4-yl)-1H-indol-3-yl)propyl]-4-[3-(acetylamino)phenyl]methylpiperazine;

(149) 1-[3-(5-(1,2,4-triazol-4-yl)-1H-indol-3-yl)propyl]-4-[4-(acetylamino)phenyl]methylpiperazine;

(150) 1-[4-(5-(1,2,4-triazol-4-yl)-1H-indol-3-yl)butyl]-4-[4-(acetylamino)phenyl]methylpiperazine;

(151) 1-[3-(5-(1,2,4-triazol-4-yl)-1H-indol-3-yl)propyl]-4-(2-methoxyphenyl)methylpiperazine;

(152) 1-[3-(5-(1,2,4-triazol-4-yl)-1H-indol-3-yl)propyl]-4-benzylpiperazine;

(153) 1-[3-(5-(1,2,4-triazol-4-yl)-1H-indol-3-yl)propyl]-4-(pyridin-3-yl)methylpiperazine;

(154) 1-[3-(5-(1,2,4-triazol-4-yl)-1H-indol-3-yl)propyl]-4-(pyridin-2-yl)methylpiperazine;

(155) 1-[3-(5-(1,2,4-triazol-4-yl)-1H-indol-3-yl)propyl]-4-(pyridin-4-yl)methylpiperazine;

(156) (3R)-3-benzyloxymethyl-1-[2-(5-(1,2,4-triazol-4-yl)-1H-indol-3-yl)ethyl]pyrrolidine;

(157) (3S)-3-(N-benzyl-N-methyl)aminomethyl-1-[2-(5-(1,2,4-triazol-4-yl)-1H-indol-3-yl)ethyl]pyrrolidine;

(158) (2S)-2-(N-benzyl-N-methyl)aminomethyl-1-[2-(5-(1,2,4-triazol-4-yl)-1H-indol-3-yl)ethyl]pyrrolidine;

(159) (3S)-3-(N-benzyl)aminomethyl-1-[2-(5-(1,2,4-triazol-4-yl)-1H-indol-3-yl)ethyl]pyrrolidine;

(160) 4-(4-acetylaminophenyl)methylamino-1-[3-(5-(1,2,4-triazol-4-yl)-1H-indol-3-yl)propyl]piperidine;

(161) 1-[3-(5-(imidazol-1-yl)-1H-indol-3-yl)propyl]-4-[(R)-α-(methoxymethyl)benzylamino]piperidine;

(162) 1-[3-(5-(1,2,4-triazol-1-ylmethyl)-1H-indol-3-yl)propyl]-4-[(R)-1-(4-fluorophenyl)-2-methoxyethylamino]piperidine;

(163) 1-[3-(5-(1,2,4-triazol-1-ylmethyl)-1H-indol-3-yl)propyl]-4-[N-(4-fluorobenzyl)-N-methylamnino]piperidine;

(164) 1-[3-(5-(1,2,4-triazol-4-yl)-1H-indol-3-yl)propyl]-4-(2-phenylpiperidin-1-yl)piperidine;

(165) 1-[3-(5-(1,2,4-triazol-4-yl)-1H-indol-3-yl)propyl]-4-[(R)-1-(4-fluorophenyl)-2-methoxyethylamino]piperidine;

(166) 1-[3-(5-(1,2,4-triazol-4-yl)-1H-indol-3-yl)propyl]-4-(indan-1-ylaminomethyl)piperidine;

(167) 1-[3-(5-(1,2,4-triazol-4-yl)-1H-indol-3-yl)propyl]-4-[N-(R)-α-(hydroxymethyl)benzyl]-N-methylaminomethyl]piperidine;

(168) (3R)-3-(benzylthio)methyl-1-[2-(5-(1,2,4-triazol-4-yl)-1H-indol-3-yl)ethyl]pyrrolidine;

(169) (±)-1-[3-(5-(1,2,4-triazol-4-yl)-1H-indol-3-yl)propyl]-4-(1-benzylamino-2-hydroxyethyl)piperidine;

(170) 1-[3-(5-(1,2,4-triazol-1-yl)-1H-indol-3-yl)propyl]-4-[(R)-α-(hydroxymethyl)benzylamino]piperidine;

(171) 1-[3-(5-(imidazol-1-yl)-1H-indol-3-yl)propyl]-4-[(R)-α-(methyl)benzylamino]piperidine;

(172) 1-[3-(5-(imidazol-1-yl)-1H-indol-3-yl)propyl]-4-[(R)-α-(hydroxymethyl)benzylamino]piperidine;

(173) 1-[3-(5-(1,2,4-triazol-1-ylmethyl)-1H-indol-3-yl)propyl]-4-[(R)-α-(hydroxymethyl)benzylamino]piperidine;

(174) 1-[3-(5-(1,2,4-triazol-4-yl)-1H-indol-3-yl)propyl]-4-[(R)-α-(methoxymethyl)benzylamino]piperidine;

(175) 1-[3-(5-(1,2,4-triazol-4-yl)-1H-indol-3-yl)propyl]-4-[N-(R)-α-(methoxymethyl)benzyl-N-methylamino]piperidine;

(176) (3R)-3-benzyloxy-1-[2-(5-(1,2,4-triazol-4-yl)-1H-indol-3-yl)ethyl]pyrrolidine;

(177) (3R)-3-(4-methoxyphenyl)methoxy-1-[2-(5-(1,2,4-triazol-4-yl)-1H-indol-3-yl)ethyl]pyrrolidine;

(178) (3R)-3-(pyridin-3-yl)methoxy-1-[2-(5-(1,2,4-triazol-4-yl)-1H-indol-3-yl)ethyl]pyrrolidine;

(179) (3R)-3-benzyloxymethyl-1-[2-(5-(1,2,4-triazol-4-yl)-1H-indol-3-yl)ethyl]pyrrolidine;

(180) (3S)-3-(N-benzyl-N-methyl)aminomethyl-1-[2-(5-(1,2,4-triazol-4-yl)-1H-indol-3-yl)ethyl]pyrrolidine;

(181) (2S)-2-(N-benzyl-N-methyl)aminomethyl-1-[2-(5-(1,2,4-triazol-4-yl)-1H-indol-3-yl)ethyl]pyrrolidine;

(182) (3S)-3-(N-benzyl)aminomethyl-1-[2-(5-(1,2,4-triazol-4-yl)-1H-indol-3-yl)ethyl]pyrrolidine;

(183) 4-(4-acetylaminophenyl)methylamino-1-[3-(5-(1,2,4-triazol-4-yl)-1H-indol-3-yl)propyl]piperidine;

(184) 4-benzylamino-1-[3-(5-(1,2,4-triazol-4-yl)-1H-indol-3-yl)propyl]piperidine;

(185) 4-(N-benzyl-N-methyl)amino-1-[3-(5-(1,2,4-triazol-4-yl)-1H-indol-3-yl)propyl]piperidine;

(186) 4-(N-benzyl-N-methyl)aminomethyl1-[3-(5-(1,2,4-triazol-4-yl)-1H-indol-3-yl)propyl]piperidine;

(187) 1-[3-(5-(1,2,4-triazol-4-yl)-1H-indol-3-yl)propyl]-4-[α-(methyl)benzylamino]piperidine;

(188) 1-[3-(5-(1,2,4-triazol-4-yl)-1H-indol-3-yl)propyl]-4-[α-(hydroxymethyl)benzylamino]piperidine;

(189) 1-[3-(5-(1,2,4-triazol-4-yl)-1H-indol-3-yl)propyl]-4-[(1-hydroxymethyl-2-phenyl)ethylamino]piperidine;

(190) 4-(N-benzyl)aminomethyl-1-[3-(5-(1,2,4-triazol-4-yl)-1H-indol-3-yl)propyl]piperidine;

(191) 1-[3-(5-(1,2,4-triazol-4-yl)-1H-indol-3-yl)propyl]-4-[(2-hydroxy-1-methyl-2-phenyl)ethylamino]piperidine;

(192) 1-[3-(5-(1,2,4-triazol-4-yl)-1H-indol-3-yl)propyl]-4-[2-(4-acetylaminophenyl)ethylamino]piperidine;

(193) 1-[3-(5-(1,2,4-triazol-4-yl)-1H-indol-3-yl)propyl]-4-[(α-(methyl)benzylamino]methylpiperidine;

(194) 1-[3-(5-(1,2,4-triazol-4-yl)-1H-indol-3-yl)propyl]-4-[1-(4-acetylaminophenyl)ethylamino]methylpiperidine;

(195) 1-[3-(5-(1,2,4-triazol-4-yl)-1H-indol-3-yl)propyl]-4-[N-[α-(hydroxymethyl)benzyl]-N-methylamino]piperidine;

(196) 1-[3-(5-(1,2,4-triazol-4-yl)-1H-indol-3-yl)propyl]-4-[N-(2-(4-acetylaminophenyl)ethyl)-N-methylamino]piperidine;

(197) 1-[3-(5-(1,2,4-triazol-4-yl)-1H-indol-3-yl)propyl]-4-[N-(4-acetylaminobenzyl)-N-methylamino]methylpiperidine;

(198) 1-[3-(5-(1,2,4-triazol-4-yl)-1H-indol-3-yl)propyl]-4-[N-(thien-2-yl)methyl-N-methylamino]piperidine;

(199) 1-[3-(5-(1,2,4-triazol-4-yl)-1H-indol-3-yl)propyl]-4-[(R)-α-(hydroxymethyl)benzylamino]methylpiperidine;

(200) 3-(4-acetylaminobenzyl)aminomethyl-1-[2-(5-(1,2,4-triazol-4-yl)-1H-indol-3-yl)ethyl]pyrrolidine;

(201) (3R)-3-(N-benzyl)aminomethyl-1-[2-(5-(1,2,4-triazol-4-yl)-1H-indol-3-yl)ethyl]pyrrolidine;

(202) (3S)-3-(pyridin-4-ylmethyl)aminomethyl-1-[2-(5-(1,2,4-triazol-4-yl)-1H-indol-3-yl)ethyl]pyrrolidine;

(203) 3-(N-benzyl)aminomethyl-1-[2-(5-(1,2,4-triazol-4-yl)-1H-indol-3-yl)ethyl]azetidine;

(204) 4-benzyl-4-hydroxy-1-[3-(5-(1,2,4-triazol-4-yl)-1H-indol-3-yl)propyl]piperidine;

(205) 3-(N-benzyl)aminomethyl-1-[3-(5-(1,2,4-triazol-4-yl)-1H-indol-3-yl)propyl]azetidine;

(206) 4-(N-benzyl)aminomethyl-4-hydroxy-1-[3-(5-(1,2,4-triazol-4-yl)-1H-indol-3-yl)propyl]piperidine;

(207) 4-(N-benzyl-N-methyl)aminomethyl-4-hydroxy-1-[3-(5-(1,2,4-triazol-4-yl)-1H-indol-3-yl)propyl]piperidine;

(208) 3-(N-benzyl-N-methyl)aminomethyl-1-[2-(5-(1,2,4-triazol-4-yl)-1H-indol-3-yl)ethyl]azetidine;

(209) (3S)-3-[N-α-(methyl)benzyl]aminomethyl-1-[2-(5-(1,2,4-triazol-4-yl)-1H-indol-3-yl)ethyl]pyrrolidine;

(210) (3S)-3-[N-(furan-3-ylmethyl)amino]methyl-1-[2-(5-(1,2,4-triazol-4-yl)-1H-indol-3-yl)ethyl]pyrrolidine;

(211) (3S)-3-[N-(furan-2-ylmethyl)amino]methyl-1-[2-(5-(1,2,4-triazol-4-yl)-1H-indol-3-yl)ethyl]pyrrolidine;

(212) (3S)-3-[N-α-(hydroxymethyl)benzyl]aminomethyl-1-[2-(5-(1,2,4-triazol-4-yl)-1H-indol-3-yl)ethyl]pyrrolidine;

(213) (3S)-3-[N-benzyl-N-(2-hydroxy)ethyl]aminomethyl-1-[2-(5-(1,2,4-triazol-4-yl)-1H-indol-3-yl)ethyl]pyrrolidine;

(214) (3S)-3-[N-(2-phenylethyl)amino]methyl-1-[2-(5-(1,2,4-triazol-4-yl)-1H-indol-3-yl)ethyl]pyrrolidine;

(215) (3S)-3-[N-(2-phenylethyl)-N-methylamino]methyl-1-[2-(5-(1,2,4-triazol-4-yl)-1H-indol-3-yl)ethyl]pyrrolidine;

(216) (3S)-3-(N-α-dimethylbenzyl)aminomethyl-1-[2-(5-(1,2,4-triazol-4-yl)-1H-indol-3-yl)ethyl]pyrrolidine;

(217) (3S)-3-[N-(S)-α-methylbenzyl]aminomethyl-1-[2-(5-(1,2,4-triazol-1-yl)-1H-indol-3-yl)ethyl]pyrrolidine;

(218) (3S)-3-[N-(R)-α-(hydroxymethyl)benzyl]aminomethyl-1-[2-(5-(1,2,4-triazol-1-yl)-1H-indol-3-yl)ethyl]pyrrolidine;

(219) (3S)-3-(N-benzyl)aminomethyl-1-[2-(5-(1,2,4-triazol-1-ylmethyl)-1H-indol-3-yl)ethyl]pyrrolidine;

(220) (3S)-3-[N-(S)-α-methylbenzyl]aminomethyl-1-[2-(5-(1,2,4-triazol-1-ylmethyl)-1H-indol-3-yl)ethyl]pyrrolidine;

(221) (3S)-3-[N-(R)-α-(hydroxymethyl)benzyl]aminomethyl-1-[2-(5-(1,2,4-triazol-1-ylmethyl)-1H-indol-3-yl)ethyl]-pyrrolidine;

(222) (3S)-3-(N-benzyl-N-methyl)aminomethyl-1-[2-(5-(imidazol-1-yl)-1H-indol-3-yl)ethyl]pyrrolidine;

(223) (3S)-3-(N-benzyl-N-methyl)aminomethyl-1-[2-(5-(1,2,4-triazol-1-ylmethyl)-1H-indol-3-yl)ethyl]pyrrolidine;

(224) (3R)-3-[N-methyl-N-(S)-α-methylbenzyl]aminomethyl-1-[2-(5-(1,2,4-triazol-1-ylmethyl)-1H-indol-3-yl)ethyl]-pyrrolidine;

(225) (3R)-3-[N-methyl-N-(R)-α-hydroxymethylbenzyl]amino-methyl-1-[2-(5-(1,2,4-triazol-1-ylmethyl)-1H-indol-3-yl)ethyl]pyrrolidine;

(226) (3R)-3-[N-methyl-N-(S)-α-methylcyclohexylmethyl]-aminomethyl-1-[2-(5-(1,2,4-triazol-1-ylmethyl)-1H-indol-3-yl)ethyl]pyrrolidine;

(227) (3R)-3-[3-(R)-hydroxy-2-(R)-phenylpiperidin-1-yl]methyl-1-[2-(5-(1,2,4-triazol-1-ylmethyl)-1H-indol-3-yl)ethyl]-pyrrolidine;

(228) (3R)-3-[3-(R)-hydroxy-2-(R)-phenylpiperidin-1-yl]methyl-1-[2-(5-(1,2,4-triazol-1-yl)-1H-indol-3-yl)ethyl]pyrrolidine;

(229) 4-hydroxy-4-(phenylsulfinyl)methyl-1-[3-(5-(1,2,4-triazol-4-yl)-1H-indol-3-yl)propyl]piperidine;

(230) (3R)-3-[2-(R,S)-phenylpiperidin-1-yl]methyl-1-[2-(5-(1,2,4-triazol-1-ylmethyl)-1H-indol-3-yl)ethyl]pyrrolidine;

(231) 4-(3,3-dimethylpiperidin-1-yl)methyl-4-hydroxy-1-[3-(5-(1,2,4-triazol-4-yl)-1H-indol-3-yl)propyl]piperidine;

(232) 4-hydroxy-4-(1,2,3,4-tetrahydroisoquinolin-2-yl)methyl-1-[3-(5-(1,2,4-triazol-4-yl)-1H-indol-3-yl)propyl]piperidine;

(233) 4-hydroxy-4-(N-isobutyl-N-methyl)aminomethyl-1-[3-(5-(1,2,4-triazol-4-yl)-1H-indol-3-yl)propyl]piperidine;

(234) 4-[N-benzyl-N-(2-hydroxyethyl)amino]methyl-4-hydroxy-1-[3-(5-(1,2,4-triazol-4-yl)-1H-indol-3-yl)propyl]-piperidine;

(235) 4-[N-(2,2-dimethylpropyl)-N-methylamino]methyl-4-hydroxy-1-[3-(5-(1,2,4-triazol-4-yl)-1H-indol-3-yl)propyl]piperidine;

(236) 4-[N-(R)-α-hydroxymethylbenzyl-N-methylamino]methyl-4-hydroxy-1-[3-(5-(1,2,4-triazol-4-yl)-1H-indol-3-yl)propyl]piperidine;

(237) 4-hydroxy-4-(2-pyridylmethyl)aminomethyl-1-[3-(5-(1,2,4-triazol-4-yl)-1H-indol-3-yl)propyl]piperidine;

(238) 4-hydroxy-4-(2-methylphenylmethyl)aminomethyl-1-[3-(5-(1,2,4-triazol-4-yl)-1H-indol-3-yl)propyl]piperidine;

47

(239) 4-hydroxy-4-[N-(2-methylphenylmethyl)-N-methylamino]methyl-1-[3-(5-(1,2,4-triazol-4-yl)-1H-indol-3-yl)propyl]piperidine;

(240) 3-(benzylamino)methyl-3-hydroxy-1-[3-(5-(1,2,4-triazol-4-yl)-1H-indol-3-yl)propyl]pyrrolidine;

(241) 3-(benzylamino)methyl-3-hydroxy-1-[2-(5-(1,2,4-triazol-4-yl)-1H-indol-3-yl)ethyl]pyrrolidine;

(242) 1-[3-(5-(1,2,4-triazol-4-yl)-1H-indol-3-yl)propyl]-4-[(R)-α-(carbamoyl-oxymethyl)benzylamino]piperidine;

(243) 1-[3-(5-(1,2,4-triazol-4-yl)-1H-indol-3-yl)propyl]-4-[(1R,2S)-2-hydroxy-1-phenylpropylamino]piperidine;

(244) 1-[3-(5-(1,2,4-triazol-4-yl)-1H-indol-3-yl)propyl]-4-[(1R,2R)-2-hydroxy-1-phenylpropylamino]piperidine;

(245) 1-[3-(5-(1,2,4-triazol-4-yl)-1H-indol-3-yl)propyl]-4-[(R,S)-1-hydroxy-2-phenylprop-2-ylamino]piperidine;

(246) 1-[3-(5-(1,2,4-triazol-4-yl)-1H-indol3-yl)propyl]-4-[(R)-2-hydroxy-1-(4-fluorophenyl)ethylamino]piperidine;

(247) 1-[3-(5-(1,2,4-triazol-4-yl)-1H-indol-3-yl)propyl]-4-[(1R,2R)-2-hydroxyindan-1-ylamino)piperidine;

(248) 1-[3-(5-(1,2,4-triazol-4-yl)-1H-indol-3-yl)propyl]-4-[(R,S)-indan-1-ylamino]piperidine;

(249) 1-[3-(5-(1,2,4-triazol-4-yl)-1H-indol-3-yl)propyl]-4-[(R,S)-1-(4-fluorophenyl)ethylamnino]piperidine;

(250) 1-[3-(5-(1,2,4-triazol-4-yl)-1H-indol-3-yl)propyl]-4-[(R)-1-phenylprop-2-ylamino]piperidine;

(251) 1-[3-(5-(1,2,4-triazol-4-yl)-1H-indol-3-yl)propyl]-4-[N-(thien-3-ylmethyl)-N-methylamino]piperidine;

(252) 1-[3-(5-(1,2,4-triazol-4-yl)-1H-indol-3-yl)propyl]-4-[N-(furan-3-ylmethyl)-N-methylamino]piperidine;

(253) 1-[3-(5-(1,2,4-triazol-4-yl)-1H-indol-3-yl)propyl]-4-(furan-3-ylmethyl)aminopiperidine;

(254) 1-[3-(5-(1,2,4-triazol-4-yl)-1H-indol-3-yl)propyl]-4-[N,N-di-(furan-3-ylmethyl)amino]piperidine;

(255) 1-[3-(5-(1,2,4-triazol-4-yl)-1H-indol-3-yl)propyl]-4-[N-(3,3-dimethylallyl)-N-methylamino]piperidine;

(256) 1-[3-(5-(1,2,4-triazol-4-yl)-1H-indol-3-yl)propyl]-4-(N-allyl-N-methylamino)piperidine;

(257) N,N-Dimethyl-2-[5-(1,2,4-triazol-1-ylmethyl)-1H-indol-3-yl]ethylamine;

(258) N,N-Dimethyl-2-[5-(1,3-imidazol-1-ylmethyl)-1H-indol-3-yl]ethylamine;

(259) N,N-Dimethyl-2-[5-(5-methyl-1,2,3,4-triazol-1-ylmethyl)-1H-indol-3-yl]ethylamine;

(260) N,N-Dimethyl-2-[5-(1,3,4-triazol-1-ylmethyl)-1H-indol-3-yl]ethylamine;

(261) N,N-Dimethyl-2-[5-(1,3,4-triazol-1-yl)-1H-indol-3-yl]ethylamine;

(262) N,N-Diethyl-2-[5-(1,2,4-triazol-1-ylmethyl)-1H-indol-3-yl]ethylamine;

(263) N,N-Diethyl-2-[5-(1,3-imidazol-1-ylmethyl)-1H-indol-3-yl]ethylamine;

(264) N,N-Diethyl-2-[5-(5-methyl-1,2,3,4-tetrazol-1-ylmethyl)-1H-indol-3-yl]ethylamine;

48

(265) N,N-Diethyl-2-[5-(1,3,4-triazol-1-ylmethyl)-1H-indol-3-yl]ethylamine;

(266) N,N-Diethyl-2-[5-(1,3,4-triazol-1-yl)-1H-indol-3-yl]ethylamine;

(267) N,N-Dimethyl-[5-(1,2,4-triazol-1-ylmethyl)-1H-indol-3-yl]methylamine;

(268) N,N-Dimethyl-[5-(1,3-imidazol-1-ylmethyl)-1H-indol-3-yl]methylamine;

(269) N,N-Dimethyl-[5-(5-methyl-1,2,3,4-tetrazol-1-ylmethyl)-1H-indol-3-yl]methylamine;

(270) N,N-Dimethyl -[5-(1,3,4-triazol-1-ylmethyl)-1H-indol-3-yl]methylamine;

(271) N,N-Dimethyl-[5-(1,3,4-triazol-1-yl)-1H-indol-3-yl]methylamine;

(272) N,N-Diethyl-3-[5-(1,2,4-triazol-1-ylmethyl)-1H-indol-3-yl]propylamine;

(273) N,N-Dimethyl-3-[5-(1,3-imidazol-1-ylmethyl)-1H-indol-3-yl]propylamine;

(274) N,N-Diethyl-3-[5-(5-methyl-1,2,3,4-tetrazol-1-ylmethyl)-1H-indol-3-yl]propylamine;

(275) N,N-Dimethyl-3-[5-(1,3,4-triazol-1-ylmethyl)-1H-indol-3-yl]propyl-amine;

(276) N,N-Diethyl-3-[5-(1,3,4-triazol-1-yl)-1H-indol-3-yl]propylamine;

(277) N,N-Dimethyl-4-[5-(3-methyl-1,2,4,5-tetrazol-1-ylmethyl)-1H-indol-3-yl]butylamine;

(278) N,N-Dimethyl-4-[5-(2-ethyl-1,3-ethyl-imidazol-1-ylmethyl)-1H-indol-3-yl]butylamine;

(279) N,N-Dimethyl-4-[5-(5-ethyl-1,2,3,4-triazol-1-ylmethyl)-1H-indol-3-yl]butylamine;

(280) N,N-Dimethyl-4-[5-(2-methyl-1,3,4-triazol-1-ylmethyl)-1H-indol-3-yl]butylamine;

(281) N,N-Dimethyl-4-[5-(2-ethyl-1,3,4-triazol-1-yl)-1H-indol-3-yl]butylamine;

(282) 2-[5-(1,2,4-triazol-1-ylmethyl)-1H-indol-3-yl]ethylalcohol;

(283) 2-[5-(1,3-imidazol-1-ylmethyl)-1H-indol-3-yl]ethylalcohol;

(284) 2-[5-(5-methyl-1,2,3,4-tetrazol-1-ylmethyl)-1H-indol-3-yl]ethylalcohol;

(285) 2-[5-(1,3,4-triazol-1-ylmethyl)-1H-indol-3-yl]ethylalcohol;

(286) 2-[5-(1,3,4-triazol-1-yl)-1H-indol-3-yl]ethylalcohol;

(287) [5-(1,2,4-triazol-1-ylmethyl)-1H-indol-3-yl]-methylalcohol;

(288) 3-[5-(1,3-imidazol-1-ylmethyl)-1H-indol-3-yl]propylalcohol;

(289) 4-[5-(5-methyl-1,2,3,4-tetrazol-1-ylmethyl)-1H-indol-3-yl]butylalcohol;

(290) 2-[5-(2-methyl-1,3,4-triazol-1-ylmethyl)-1H-indol-3-yl]ethylalcohol; and (291) 2-[5-(5-methyl-1,3,4-triazol-1-yl)-1H-indol-3-yl]ethylalcohol.

20. The process according to claim 18 wherein the compound of structural formula IV is selected from:

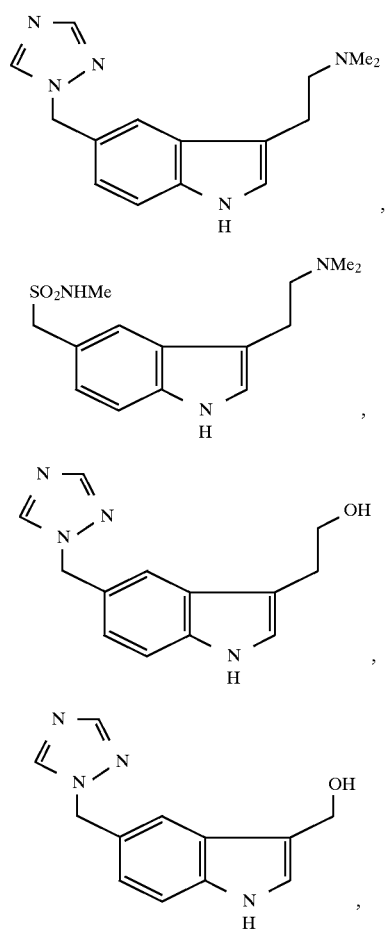
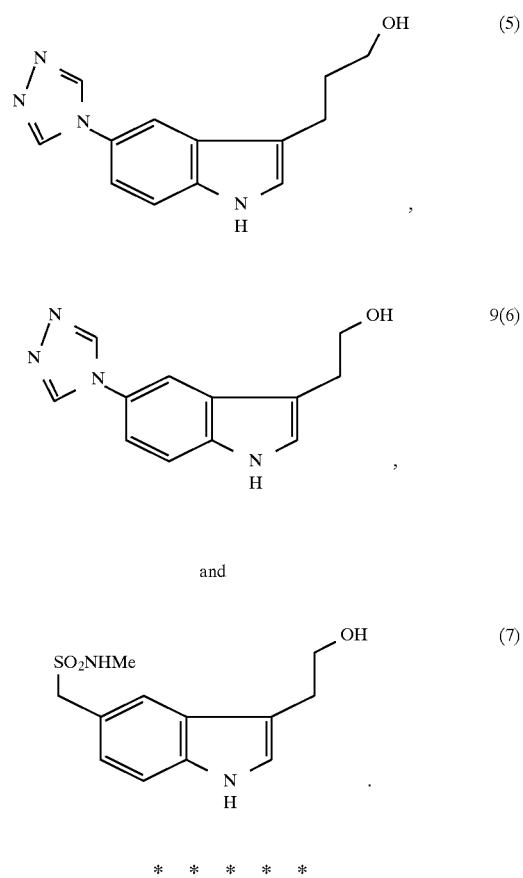
* * * * *